(12) United States Patent
Chen et al.

(10) Patent No.: US 12,421,252 B2
(45) Date of Patent: Sep. 23, 2025

(54) SPIRO (ISOBENZOFURANAZETIDINE) COMPOUNDS FOR THE TREATMENT OF AUTOIMMUNE DISEASE

(71) Applicant: Hoffmann-La Roche Inc., Little Falls, NJ (US)

(72) Inventors: Jianguo Chen, Shanghai (CN); Weixing Zhang, Shanghai (CN); Zhisen Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 681 days.

(21) Appl. No.: 17/756,221

(22) PCT Filed: Nov. 18, 2020

(86) PCT No.: PCT/EP2020/082567
§ 371 (c)(1),
(2) Date: May 19, 2022

(87) PCT Pub. No.: WO2021/099406
PCT Pub. Date: May 27, 2021

(65) Prior Publication Data
US 2023/0002415 A1 Jan. 5, 2023

(51) Int. Cl.
*C07D 519/00* (2006.01)
*C07D 491/107* (2006.01)
*C07D 491/147* (2006.01)

(52) U.S. Cl.
CPC ....... *C07D 519/00* (2013.01); *C07D 491/107* (2013.01); *C07D 491/147* (2013.01)

(58) Field of Classification Search
CPC .............. C07D 519/00; C07D 491/107; C07D 491/147
See application file for complete search history.

(56) References Cited

U.S. PATENT DOCUMENTS

| | | | |
|---|---|---|---|
| 2019/0185469 A1 | 6/2019 | Dyckman et al. | |
| 2021/0253575 A1 | 8/2021 | Dey et al. | |
| 2021/0269451 A1 | 9/2021 | Liu et al. | |
| 2021/0300924 A1 | 9/2021 | Liu et al. | |
| 2021/0300947 A1 | 9/2021 | Dey et al. | |
| 2021/0323977 A1 | 10/2021 | Liu et al. | |
| 2021/0340134 A1 | 11/2021 | Qui et al. | |
| 2021/0340136 A1 | 11/2021 | Zhu et al. | |
| 2021/0355122 A1 | 11/2021 | Dey et al. | |
| 2021/0395239 A1 | 12/2021 | Dey et al. | |
| 2022/0112187 A1 | 4/2022 | Liu et al. | |
| 2022/0363665 A1 | 11/2022 | Dey et al. | |

FOREIGN PATENT DOCUMENTS

| EP | 3 623 369 A1 | 3/2020 |
|---|---|---|
| WO | 2015/057655 A1 | 4/2015 |
| WO | 2015/057659 A1 | 4/2015 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/047081 A1 | 3/2018 |
| WO | 2018/049089 A1 | 3/2018 |
| WO | 2019/018354 A1 | 1/2019 |
| WO | 2019/028301 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |
| WO | 2019/238616 A1 | 12/2019 |
| WO | 2019/238629 A1 | 12/2019 |
| WO | 2020/043271 A1 | 3/2020 |

(Continued)

OTHER PUBLICATIONS

Alper, P., et al., "Discovery of potent, orally bioavailable in vivo efficacious antagonists of the TLR7/8 pathway" Bioorg Med Chem Lett 30(17):127366 (1-5) (Sep. 1, 2020).
International Preliminary Report on Patentability—PCT/EP2020/082567 issued May 17, 2022, pp. 1-7.
International Search Report with Written Opinion—PCT/EP2020/082567 mailed Jan. 19, 2021, pp. 1-12.
Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).

(Continued)

*Primary Examiner* — Rebecca L Anderson
(74) *Attorney, Agent, or Firm* — Bradley E. Davis

(57) ABSTRACT

The present invention relates to compounds of formula (I), wherein $R^1$, $R^3$, Y and A are as described herein, and their pharmaceutically acceptable salt, enantiomer or diastereomer thereof, and compositions including the compounds and methods of using the compounds.

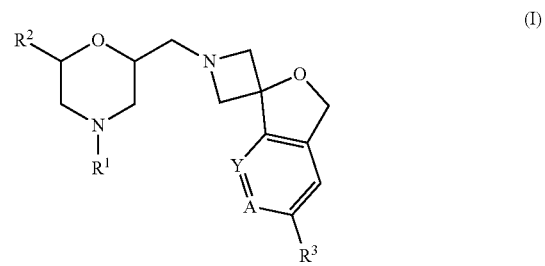

17 Claims, No Drawings

(56) References Cited

FOREIGN PATENT DOCUMENTS

| WO | 2020/048583 A1 | 3/2020 |
| WO | 2020/048595 A1 | 3/2020 |
| WO | 2020/048596 A1 | 3/2020 |
| WO | 2020/048605 A1 | 3/2020 |
| WO | 2020/052738 A1 | 3/2020 |
| WO | 2020/064792 A1 | 4/2020 |
| WO | 2020/094749 A1 | 5/2020 |
| WO | 2021/048200 A1 | 3/2021 |
| WO | 2021/052892 A1 | 3/2021 |

OTHER PUBLICATIONS

Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

USPTO et al., "U.S. Appl. No. 17/761,150, filed Mar. 16, 2022 entitled Piperidinyl Amine Compounds for the Treatment of Autoimmune Disease".

SPIRO (ISOBENZOFURANAZETIDINE) COMPOUNDS FOR THE TREATMENT OF AUTOIMMUNE DISEASE

CROSS-REFERENCE TO RELATED APPLICATIONS

This application is a National Stage Entry under 35 U.S.C. § 371 of International Application No. PCT/EP2020/082567, filed Nov. 18, 2020, which claims benefit of priority to Chinese Application No. PCT/CN2019/119737, filled Nov. 20, 2019.

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7, 8, 9 is considered as a key node in a broad of autoimmune and auto-inflammatory diseases (Krieg, A. M. et al. Immunol. Rev. 2007, 220, 251. Jiménez-Dalmaroni, M. J. et al Autoimmun Rev. 2016, 15, 1. Chen, J. Q., et al. Clinical Reviews in Allergy & Immunology 2016, 50, 1). Anti-RNA and anti-DNA antibodies are well established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8, and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I) and (Ia),

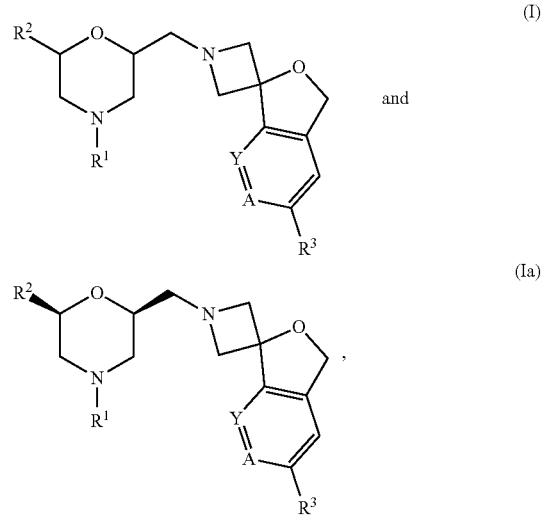

wherein
$R^1$ is

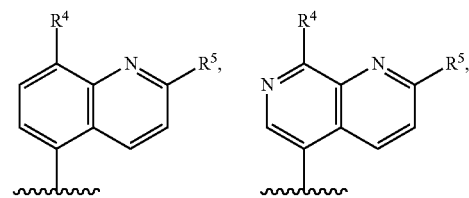

-continued

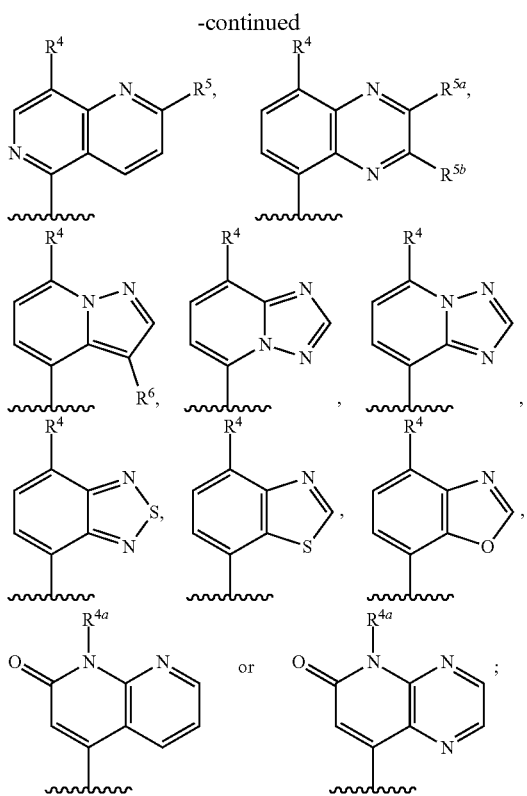

wherein R[4] is C$_{1-6}$ alkyl, C$_{1-6}$alkoxy, haloC$_{1-6}$alkyl, halogen, nitro or cyano; R[4a] is C$_{1-6}$alkyl or C$_{3-7}$cycloalkyl; R[5], R[5a] and R[5b] are independently selected from H and deuterium; R[6] is H or halogen;

R[2] is C$_{1-6}$ alkyl;

R[3] is unsubstituted or substituted heterocyclyl;

Y and A are independently selected from CH and N;

or a pharmaceutically acceptable salt thereof.

Another object of the present invention is related to novel compounds of formula (I) or (Ia), their manufacture, medicaments based on a compound in accordance with the invention and their production as well as the use of compounds of formula (I) or (Ia) as TLR7 and/or TLR8 and/or TLR9 antagonist, and for the treatment or prophylaxis of systemic lupus erythematosus or lupus nephritis. The compounds of formula (I) or (Ia) show superior TLR7 and/or TLR8 and/or TLR9 antagonism activity. In addition, the compounds of formula (I) or (Ia) also show good hPBMC, cytotoxicity, solubility, human microsome stability and SDPK profiles, as well as low CYP inhibition.

DETAILED DESCRIPTION OF THE INVENTION

Definitions

The term "C$_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "C$_{1-6}$alkyl" groups are methyl, ethyl and n-propyl.

The term "C$_{3-7}$cycloalkyl" denotes a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" groups are cyclopropyl, cyclopentyl and cyclohexyl.

The term "halogen" and "halo" are used interchangeably herein and denote fluoro, chloro, bromo, or iodo.

The term "C$_{1-6}$ alkoxy" denotes C$_{1-6}$alkyl-O—.

The term "halopyrrolidinyl" denotes a pyrrolidinyl substituted once, twice or three times by halogen. Examples of halopyrrolidinyl include, but not limited to, difluoropyrrolidinyl and fluoropyrrolidinyl.

The term "heterocyclyl" or "heterocyclic" denotes a monovalent saturated or partly unsaturated mono or bicyclic ring system of 3 to 12 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl. Examples for bicyclic saturated heterocyclic ring are azabicyclo[3.2.1]octyl, quinuclidinyl, oxaazabicyclo[3.2.1]octanyl, azabicyclo[3.3.1]nonanyl, oxaaza-bicyclo[3.3.1]nonanyl, azabicyclo[3.1.0]hexanyl, oxodiazaspiro[3.4]octanyl, acetyloxodiazaspiro[3.4]octanyl, thiaazabicyclo[3.3.1]nonanyl, oxoazaspiro[2.4]heptanyl, oxoazaspiro[3.4]octanyl, oxoazabicyclo[3.1.0]hexanyl and dioxotetrahydropyrrolo[1,2-a]pyrazinyl. Examples for bicyclic heterocyclyl include, but not limited to, 1,2,3,4-tetrahydroisoquinolinyl; 5,6,7,8-tetrahydro-1,6-naphthyridinyl; 5,6,7,8-tetrahydro-1,7-naphthyridinyl; 5,6,7,8-tetrahydro-2,6-naphthyridinyl; 5,6,7,8-tetrahydro-2,7-naphthyridinyl; isoindolinyl. Examples of heterocyclyl can be further substituted by amino, C$_{1-6}$alkyl, C$_{3-7}$cycloalkyl, halogen, hydroxy or C$_{1-6}$ alkoxy.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to (i) a compound of formula (I),

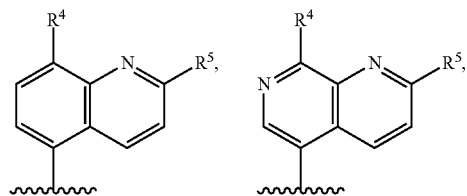

wherein
$R^1$ is

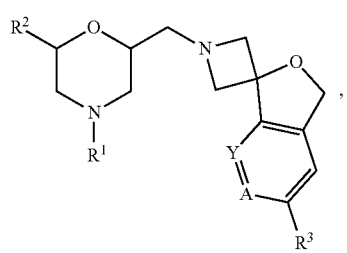

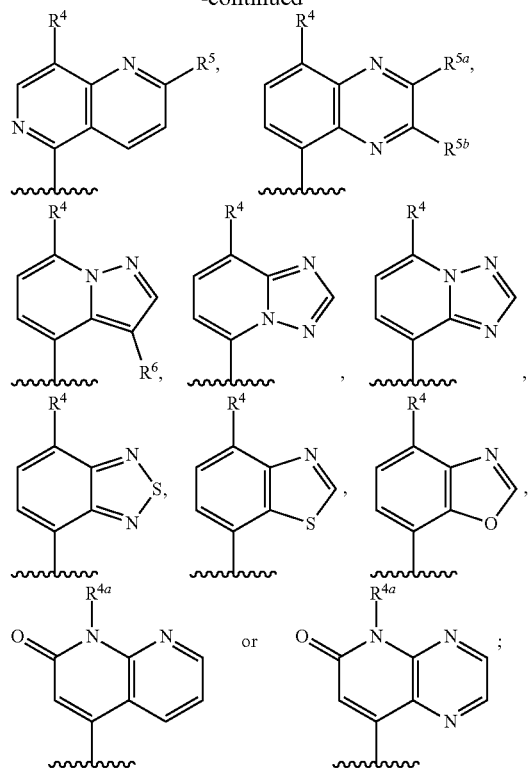

wherein $R^4$ is $C_{1-6}$ alkyl, $C_{1-6}$ alkoxy, halo$C_{1-6}$ alkyl, halogen, nitro or cyano; $R^{4a}$ is $C_{1-6}$ alkyl or $C_{3-7}$ cycloalkyl; $R^5$, $R^{5a}$ and $R^{5b}$ are independently selected from H and deuterium; $R^6$ is H or halogen;
$R^2$ is $C_{1-6}$ alkyl;
$R^3$ is unsubstituted or substituted heterocyclyl;
Y and A are independently selected from CH and N;
or a pharmaceutically acceptable salt thereof.

A further embodiment of present invention is (ii) a compound of formula (I) according to (i), wherein
$R^1$ is

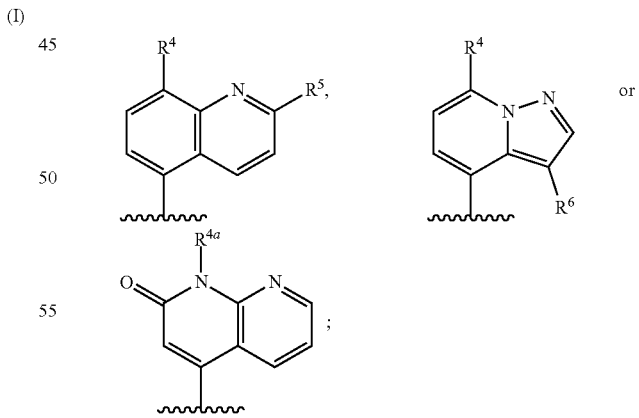

wherein $R^4$ is cyano; $R^{4a}$ is $C_{1-6}$ alkyl; $R^5$ is H or deuterium; $R^6$ is H or halogen;
$R^2$ is $C_{1-6}$ alkyl;
$R^3$ is 2,6-diazaspiro[3.3]heptanyl; 3,4,4a,5,7,7a-hexahydro-2H-pyrrolo[3,4-b][1,4]oxazinyl; 5-oxa-2,8-diazaspiro[3.5]nonanyl; amino($C_{1-6}$alkyl)azetidinyl; amino($C_{1-6}$alkyl)pyrrolidinyl; amino($C_{1-6}$ alkoxy)

pyrrolidinyl; amino(hydroxy)pyrrolidinyl; aminoazetidinyl; $C_{1-6}$alkyl-2,6-diazaspiro[3.3]heptanyl; halopyrrolidinylamino or piperazinyl;

Y and A are independently selected from CH and N provided that Y and A are not N simultaneously;

or a pharmaceutically acceptable salt thereof.

Another embodiment of present invention is (iii) a compound of formula (Ia),

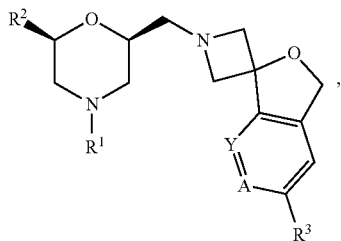
(Ia)

wherein
$R^1$ is

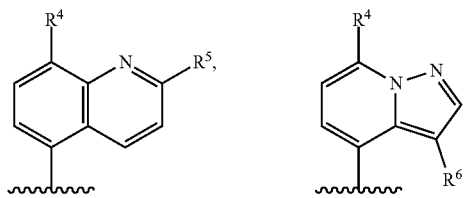

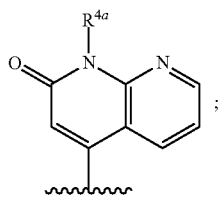

wherein $R^4$ is cyano; $R^{4a}$ is $C_{1-6}$alkyl; $R^5$ is H or deuterium; $R^6$ is H or halogen;

$R^2$ is $C_{1-6}$alkyl;

$R^3$ is 2,6-diazaspiro[3.3]heptanyl; 3,4,4a,5,7,7a-hexahydro-2H-pyrrolo[3,4-b][1,4]oxazinyl; 5-oxa-2,8-diazaspiro[3.5]nonanyl; amino($C_{1-6}$alkyl)azetidinyl; amino($C_{1-6}$alkyl)pyrrolidinyl; amino($C_{1-6}$ alkoxy) pyrrolidinyl; amino(hydroxy)pyrrolidinyl; aminoazetidinyl; $C_{1-6}$alkyl-2,6-diazaspiro[3.3]heptanyl; halopyrrolidinylamino or piperazinyl;

Y and A are independently selected from CH and N provided that Y and A are not N simultaneously;

or a pharmaceutically acceptable salt thereof.

A further embodiment of present invention is (iv) a compound of formula (I) or (Ia) according to any one of (i) to (iii), or a pharmaceutically acceptable salt thereof, wherein $R^1$ is

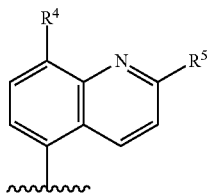 or 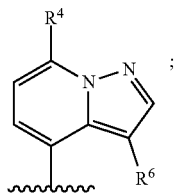 ;

wherein $R^4$ is cyano; $R^5$ is H or deuterium; $R^6$ is H or halogen.

A further embodiment of present invention is (v) a compound of formula (I) or (Ia) according to any one of (i) to (iv), or a pharmaceutically acceptable salt thereof, wherein $R^1$ is

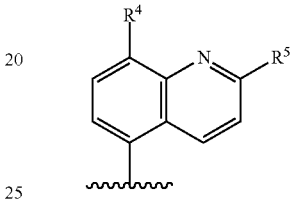 or 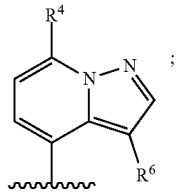 ;

wherein $R^4$ is cyano; $R^5$ is H or deuterium; $R^6$ is H or fluoro.

A further embodiment of present invention is (vi) a compound of formula (I) or (Ia) according to any one of (i) to (v), or a pharmaceutically acceptable salt thereof, wherein Y is CH and A is N; or Y is N and A is CH.

A further embodiment of present invention is (vii) a compound of formula (I) or (Ia) according to any one of (i) to (vi), or a pharmaceutically acceptable salt thereof, wherein $R^3$ is amino($C_{1-6}$alkyl)azetidinyl; 3,4,4a,5,7,7a-hexahydro-2H-pyrrolo[3,4-b][1,4]oxazinyl or amino($C_{1-6}$ alkoxy)pyrrolidinyl.

A further embodiment of present invention is (viii) a compound of formula (I) or (Ia) according to any one of (i) to (vii), or a pharmaceutically acceptable salt thereof, wherein $R^3$ is 3-amino-3-methyl-azetidin-1-yl; 3,4,4a,5,7,7a-hexahydro-2H-pyrrolo[3,4-b][1,4]oxazin-6-yl or 3-amino-4-methoxy-pyrrolidin-1-yl.

A further embodiment of present invention is (ix) a compound of formula (I) or (Ia) according to any one of (i) to (viii), wherein
$R^1$ is

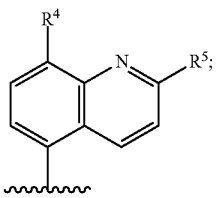 ;

wherein $R^4$ is cyano; $R^5$ is deuterium;

$R^2$ is $C_{1-6}$alkyl;

$R^3$ is amino($C_{1-6}$alkyl)azetidinyl; 3,4,4a,5,7,7a-hexahydro-2H-pyrrolo[3,4-b][1,4]oxazinyl or amino($C_{1-6}$ alkoxy)pyrrolidinyl;

Y is CH and A is N; or Y is N and A is CH;

or a pharmaceutically acceptable salt thereof.

A further embodiment of present invention is (x) a compound of formula (I) or (Ia) according to any one of (i) to (ix), wherein R¹ is

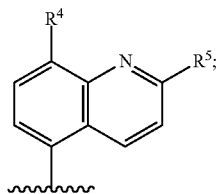

wherein R⁴ is cyano; R⁵ is deuterium;
R² is methyl;
R³ is 3-amino-3-methyl-azetidin-1-yl; 3,4,4a,5,7,7a-hexahydro-2H-pyrrolo[3,4-b][1,4]oxazin-6-yl or 3-amino-4-methoxy-pyrrolidin-1-yl;
Y is CH and A is N; or Y is N and A is CH;
or a pharmaceutically acceptable salt thereof.

Another embodiment of present invention is that (ix) compounds of formula (I) or (Ia) are selected from the following:

4-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

3-fluoro-4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile;

3-fluoro-4-[(2S,6R)-2-[[6-[[(3S,4R)-4-fluoropyrrolidin-3-yl]amino]spiro[1H-isobenzofuran-3,3'-azetidine]-1'-yl]methyl]-6-methyl-morpholin-4-yl]pyrazolo[1,5-a]pyridine-7-carbonitrile;

3-fluoro-4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile;

4-[(2S,6R)-2-[[6-[(3S)-3-amino-3-methyl-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile;

3-fluoro-4-[(2R,6S)-2-methyl-6-[(6-piperazin-1-ylspiro[1H-isobenzofuran-3,3'-azetidine]-1'-yl)methyl]morpholin-4-yl]pyrazolo[1,5-a]pyridine-7-carbonitrile;

4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile;

4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-[(3S,4S)-3-amino-4-hydroxy-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile;

5-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-2-deuterio-quinoline-8-carbonitrile;

4-[(2S,6R)-2-[[6-(2,6-diazaspiro[3.3]heptan-2-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]-1-methyl-1,8-naphthyridin-2-one;

5-[(2S,6R)-2-[[6-(3-aminoazetidin-1-yl)spiro[1H-isobenzofuran-3,3'-azetidine]-1'-yl]methyl]-6-methyl-morpholin-4-yl]-2-deuterio-quinoline-8-carbonitrile;

2-deuterio-5-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]quinoline-8-carbonitrile;

5-[(2S,6R)-2-[[6-[(3R,4R)-3-amino-4-methoxy-pyrrolidin-1-yl]spiro[1H-isobenzofuran-3,3'-azetidine]-1'-yl]methyl]-6-methyl-morpholin-4-yl]-2-deuterio-quinoline-8-carbonitrile;

5-[(2S,6R)-2-[[6-[(4aR,7aR)-3,4,4a,5,7,7a-hexahydro-2H-pyrrolo[3,4-b][1,4]oxazin-6-yl]spiro[1H-isobenzofuran-3,3'-azetidine]-1'-yl]methyl]-6-methyl-morpholin-4-yl]-2-deuterio-quinoline-8-carbonitrile;

2-deuterio-5-[(2R,6S)-2-methyl-6-[(6-piperazin-1-ylspiro[1H-isobenzofuran-3,3'-azetidine]-1'-yl)methyl]morpholin-4-yl]quinoline-8-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]pyrazolo[1,5-a]pyridine-7-carbonitrile;

5-[(2S,6R)-2-[[3-(3-aminoazetidin-1-yl)spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]-2-deuterio-quinoline-8-carbonitrile;

3-fluoro-4-[(2R,6S)-2-methyl-6-[[3-(6-methyl-2,6-diazaspiro[3.3]heptan-2-yl)spiro[5H-furo[3,4-b]pyridine-7,3'-azetidine]-1'-yl]methyl]morpholin-4-yl]pyrazolo[1,5-a]pyridine-7-carbonitrile;

5-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-2-deuterio-quinoline-8-carbonitrile;

4-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]pyrazolo[1,5-a]pyridine-7-carbonitrile;

4-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]pyrazolo[1,5-a]pyridine-7-carbonitrile;

5-[(2S,6R)-2-j[[6-[(4aR,7aR)-3,4,4a,5,7,7a-hexahydro-2H-pyrrolo[3,4-b][1,4]oxazin-6-yl]spiro[1H-furo[3,4-c]pyridine-3,3'-azetidine]-1'-yl]methyl]-6-methyl-morpholin-4-yl]-2-deuterio-quinoline-8-carbonitrile;

5-[(2S,6R)-2-[[3-[(4aR,7aR)-3,4,4a,5,7,7a-hexahydro-2H-pyrrolo[3,4-b][1,4]oxazin-6-yl]spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[3-[(3R,4R)-3-amino-4-methoxy-pyrrolidin-1-yl]spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[6-(3-aminoazetidin-1-yl)spiro[1H-furo[3,4-c]pyridine-3,3'-azetidine]-1'-yl]methyl]-6-methyl-morpholin-4-yl]-2-deuterio-quinoline-8-carbonitrile; and 4-[(2S,6R)-2-[[3-(3-amino-3-methyl-azetidin-1-yl)spiro [5H-furo[3,4-b]pyridine-7,3'-azetidine]-1'-yl]methyl]-6-methyl-morpholin-4-yl]-3-fluoro-pyrazolo[1,5-a]pyridine-7-carbonitrile;
or a pharmaceutically acceptable salt, enantiomer or diastereomer thereof.

A number of compounds used as reference herein were disclosed in patent US20150105370 showing TLR7 and TLR9 potency data summarized in table 1 (TLR8 data is not available). Compounds in Table 1 are all characterized with an aromatic ring at the terminal position (phenyl or pyridinyl). However, according to the potency data disclosed, only some of the compounds in Table 1 showed good TLR7 potency, and all of which were lack of TLR9 potency. More examples disclosed in US20150105370 with same structural characteristics confirmed such trend, which suggests the terminal aryl/heteroaryl ring is not favorable for TLR9 activity.

Meanwhile, more analogues of the compounds disclosed in US20150105370, such as compound R1, compound R2 which bear some substituents on the terminal aryl ring, were synthesized to confirm the SAR (structure-activity-relationship). But according to the potency data shown in Table 2, the substituents on the terminal aryl ring may not necessarily improve the potency of TLR9. Therefore, the skill of the art shall not obtain any incitation from the information disclosed in US20150105370 to further optimize such chemical structures.

Surprisingly, the compounds of this invention significantly improved TLR9 potency (>8 folds compared to ER-888286) while keeping excellent TLR7 and TLR8 potency. In another embodiment, hERG profile and safety ratio were greatly improved as compared with reference compounds from US20150105370 and reference compounds R1 and R2 synthesized herein (see table 3). The compounds of formula (I) or (Ia) also showed good hPBMC, cytotoxicity, solubility, human microsome stability and SDPK profiles, as well as low CYP inhibition.

TABLE 1

| TLR7 and TLR9 potency of compounds disclosed in US20150105370 | | | |
|---|---|---|---|
| Compound | Structure | HEK/hTLR7 IC50 (μM) | HEK/hTLR9 IC50 (μM) |
| ER-887258 | | 0.0852 | >2.0 |
| ER-888285 | | 0.120 | >2.0 |
| ER-888286 | | 1.370 | >2.0 |

TABLE 1-continued

TLR7 and TLR9 potency of compounds disclosed in US20150105370

| Compound | Structure | HEK/hTLR7 IC50 (μM) | HEK/hTLR9 IC50 (μM) |
|---|---|---|---|
| ER-894544 | 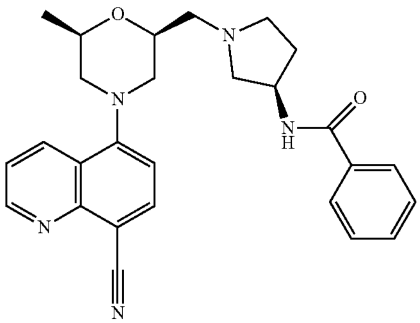 [SMILES: C[C@@H]1CN(c2ccc(C#N)c3ncccc23)C[C@H](CN2CC[C@@H](NC(=O)c3ccccc3)C2)O1] | 0.043 | >6.2 |
| ER-894160 | 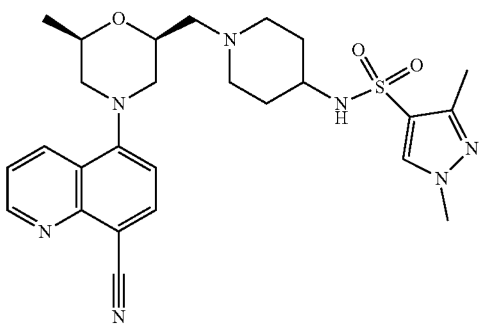 [SMILES: Cc1nn(C)cc1S(=O)(=O)NC1CCN(C[C@H]2CN(c3ccc(C#N)c4ncccc34)C[C@@H](C)O2)CC1] | 0.1990 | >10.0 |
| ER-894155 | 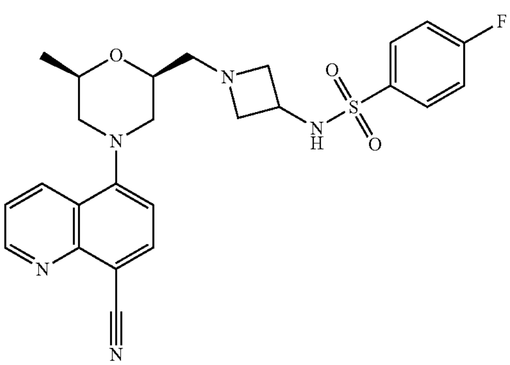 [SMILES: C[C@@H]1CN(c2ccc(C#N)c3ncccc23)C[C@H](CN2CC(NS(=O)(=O)c3ccc(F)cc3)C2)O1] | 0.2820 | >10.0 |

Synthesis

The compounds of the present invention can be prepared by any conventional means. Suitable processes for synthesizing these compounds as well as their starting materials are provided in the schemes below and in the examples. All substituents, in particular, $R^1$ to $R^6$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compound of formula (I) is shown in Scheme 1 below.

Scheme 1

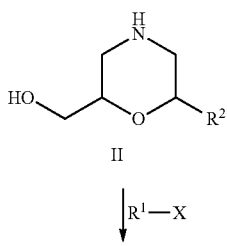

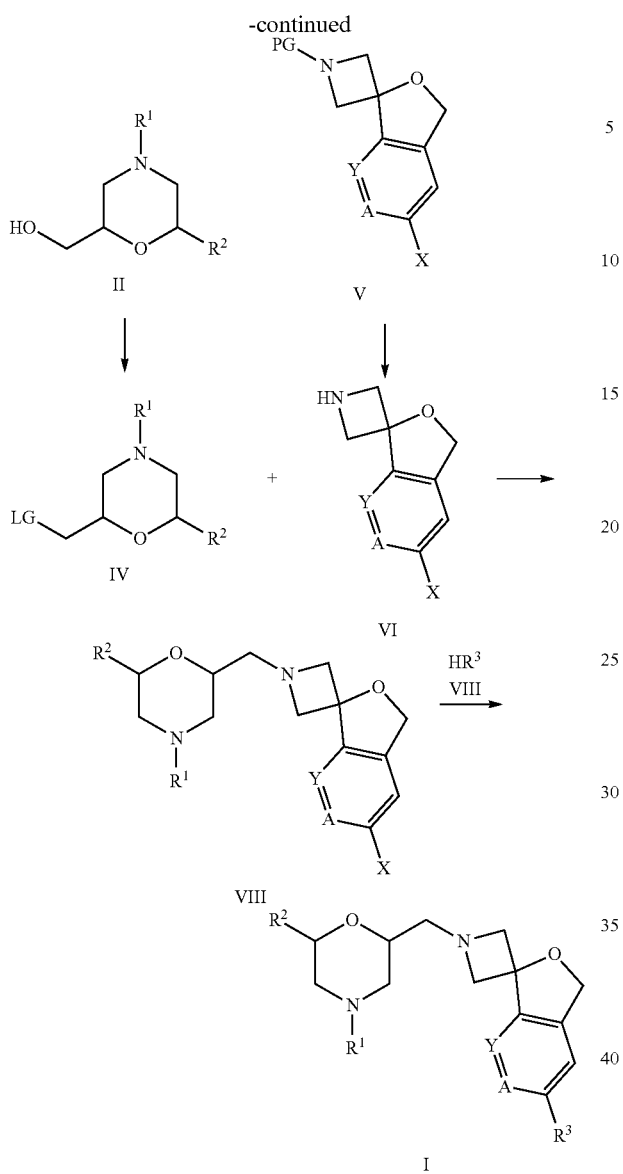

wherein X is halogen; LG is a leaving group, such as OTf, OTs and OMs; PG is a protecting group, such as Boc and Cbz.

The coupling of compound of formula (II) with $R^1$—X can be achieved in the presence of a base, such as DIPEA or $K_2CO_3$, or under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as RuPhos Pd G2, and a base, such as $Cs_2CO_3$, to provide compound of formula (III). Subsequently the hydroxy group of compound of formula (III) is converted to a leaving group, such as OTf, OTs, and OMs, under basic condition, such as DIPEA, TEA, $K_2CO_3$ and 2,6-dimethylpyridine, with $Tf_2O$, TsCl or MsCl. The protecting group of compound of formula (V) can be removed at high temperature or under acidic condition, such as TFA, or under hydrogenation condition with a catalyst, such as Pd/C and Pd(OH)$_2$/C. Compound of formula (IV) is further substituted by compound of formula (VI) in the presence of a base, such as $K_2CO_3$, DIPEA and $Cs_2CO_3$, to afford compound of formula (VII). The coupling of compound of formula (VII) with (VIII) can be achieved under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as tBuXPhos Pd G3, RuPhos Pd G2, BrettPhos Pd G3, XPhos Pd G3, Pd$_2$(dba)$_3$/BINAP and Pd$_2$(dba)$_3$/XantPhos and a base, such as $Cs_2CO_3$ or t-BuONa,to provide compound of formula (I). In some embodiment, the coupling of compound of formula (VII) with amine (VIII) may give a product containing a protecting group, e.g. Boc or Cbz, originated from (VIII), which will be removed before affording the final compound of formula (I).

Compounds of this invention can be obtained as mixtures of diastereomers or enantiomers, which can be separated by methods well known in the art, e.g. (chiral) HPLC or SFC. In another embodiment, compound of formula (Ia) can be obtained according to above scheme by using corresponding chiral starting materials.

Compounds of this invention can be obtained as mixtures of diastereomers or enantiomers, which can be separated by methods well known in the art, e.g. (chiral) HPLC or SFC.

This invention also relates to a process for the preparation of a compound of formula (I), (Ia) comprising the following step:

a) the reaction of compound of formula (VII),

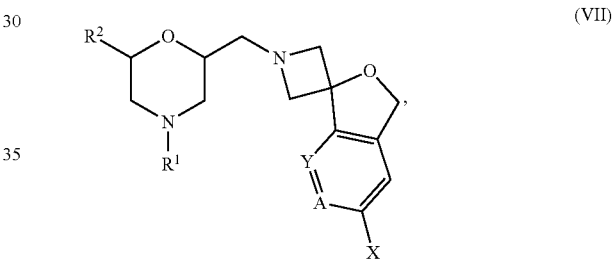

and amine HR$^3$ (VIII) via Buchwald-Hartwig amination;

wherein, X is halogen, Y and A are independently selected from CH and N.

A compound of formula (I) or (Ia) when manufactured according to the above process with achiral or chiral starting materials is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

ABBREVIATIONS

The invention will be more fully understood by reference to the following examples. They should not, however, be construed as limiting the scope of the invention.

Abbreviations used herein are as follows:
ACN: acetonitrile
$Boc_2O$: di-tert-butyl dicarbonate
$Tf_2O$: triflic anhydride
DCM: dichloromethane
DDI drug-drug-interaction
DIPEA diethylisopropylamine
EA or EtOAc: ethyl acetate
FA: formic acid
HLM human liver microsome
hr hour
hrs hours
$IC_{50}$: half inhibition concentration
LCMS liquid chromatography-mass spectrometry
LYSA lyophilisation solubility assay
MS: mass spectrometry
PE: petroleum ether
prep-HPLC: preparative high performance liquid chromatography
rt: rt
RT: retention time
RuPhos Pd G2: chloro(2-dicyclohexylphosphino-2',6'-diisopropoxy-1,1'-biphenyl)[2-(2'-amino-1,1'-biphenyl)]palladium(II) 2nd generation
SFC: supercritical fluid chromatography
TFA: trifluoroacetic acid
v/v volume ratio

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column, SunFire™ Prep-C18 (5 μm, OBD™ 30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3 \cdot H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;
Acidic condition II: A: 0.0375% TFA in $H_2O$; B: 0.01875% TFA in acetonitrile;
Basic condition I: A: 0.1% $NH_3$—$H_2O$ in $H_2O$; B: acetonitrile;
Basic condition II: A: 0.025% $NH_3$—$H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

Preparative Examples

The following examples are intended to illustrate the meaning of the present invention but should by no means represent a limitation within the meaning of the present invention:

Intermediate E

[(2R,6R)-4-(7-cyano-3-fluoro-pyrazolo[1,5-a]pyridin-4-yl)-6-methyl-morpholin-2-yl]methyl trifluoromethanesulfonate

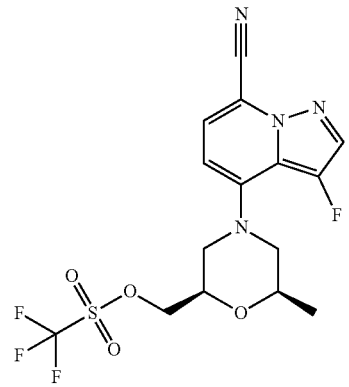 [SMILES: C[C@@H]1CN(c2ccc(C#N)n3ncc(F)c23)C[C@H](COS(=O)(=O)C(F)(F)F)O1]

The title compound was prepared according to the following scheme:

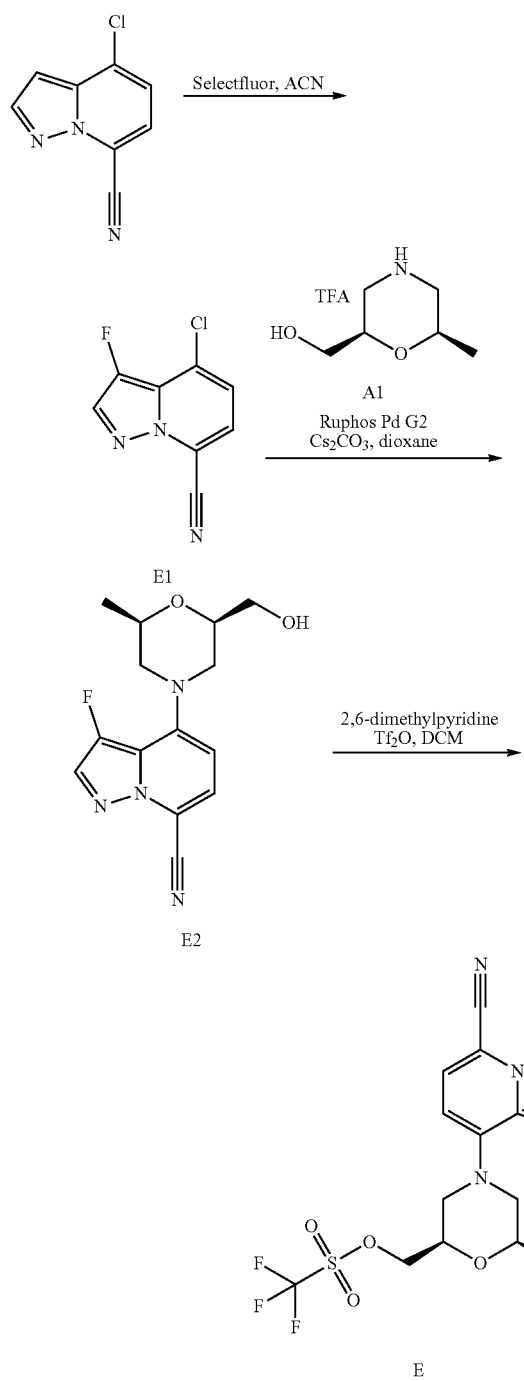

Step 1: preparation of 4-chloro-3-fluoro-pyrazolo[1,5-a]pyridine-7-carbonitrile (Compound E1)

To a solution of 4-chloropyrazolo[1,5-a]pyridine-7-carbonitrile (CAS: 1268520-74-6, Vendor: Pharmablock, 600 mg, 3.38 mmol) in acetonitrile (50 mL) was added Select-Fluor (2.39 g, 6.76 mmol). After being stirred at rt for 24 hrs, the mixture was concentrated and diluted with water (30 mL), extracted with DCM (30 mL) twice. The organic layer was washed with sat. $NH_4Cl$ and brine, dried over $Na_2SO_4$, and concentrated to give a crude product which was purified by silica gel chromatography to give compound E1 (419 mg) as a light yellow powder. MS: calc'd 196 ($MH^+$), measured 196 ($MH^+$). $^1H$ NMR (400 MHz, METHANOL-$d_4$) δ=8.17 (d, J=3.5 Hz, 1H), 7.55 (d, J=7.6 Hz, 1H), 7.35 (d, J=7.7 Hz, 1H).

Step 2: preparation of 3-fluoro-4-[(2R,6R)-2-(hydroxymethyl)-6-methyl-morpholin-4-yl]pyrazolo[1,5-a]pyridine-7-carbonitrile (compound E2)

To a solution of 4-chloro-3-fluoropyrazolo[1,5-a]pyridine-7-carbonitrile (compound E1, 419 mg, 2.14 mmol), [(2R,6R)-6-methylmorpholin-2-yl]methanol; 2,2,2-trifluoroacetic acid (compound A1, 526 mg, 2.14 mmol) and $Cs_2CO_3$ (2.79 g, 8.57 mmol) in 1,4-dioxane (10 mL) was added RuPhos Pd G2 (116 mg, 0.15 mmol) under $N_2$. The reaction mixture was heated at 90° C. for 2 hrs. After being cooled down, the mixture was diluted with EtOAc and filtered through celite. The filtrate was concentrated to give a brown oil which was purified by silica gel chromatography to give compound E2 (325 mg) as a yellow oil. MS: calc'd 291 ($MH^+$), measured 291 ($MH^+$).

Step 3: preparation of (2R,6R)-4-(7-cyanopyrazolo[1,5-a]pyridin-4-yl)-6-methyl-morpholin-2-yl]methyl trifluoromethanesulfonate (Intermediate E)

To a solution of 3-fluoro-4-[(2R,6R)-2-(hydroxymethyl)-6-methyl-morpholin-4-yl]pyrazolo[1,5-a]pyridine-7-carbonitrile (compound E2, 325 mg, 1.12 mmol) in DCM (3 mL) was added 2,6-dimethylpyridine (240 mg, 258 μL, 2.24 mmol) and $Tf_2O$ (474 mg, 284 μL, 1.68 mmol) at rt. After being stirred for 1.5 hrs, the mixture was diluted with DCM, washed with sat. $NH_4Cl$ and brine. The organic layer was dried over $Na_2SO_4$ and concentrated to give the crude product which was purified by silica gel chromatography to give Intermediate E (180 mg) as a yellow solid. MS: calc'd 423 ($MH^+$), measured 423 ($MH^+$).

Intermediate F

[(2R,6R)-4-(7-cyanopyrazolo[1,5-a]pyridin-4-yl)-6-methyl-morpholin-2-yl]methyl trifluoromethanesulfonate

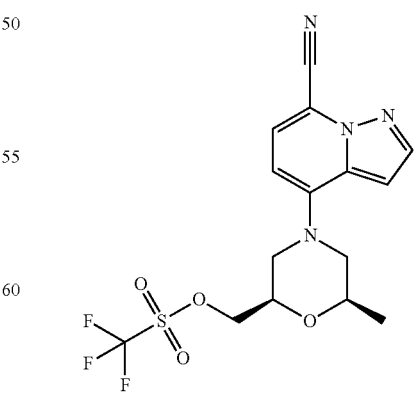

The title compound was prepared in analogy to the preparation of Intermediate E by using 4-chloropyrazolo[1, 5-a]pyridine-7-carbonitrile (CAS: 1268520-74-6, Vendor: PharmaBlock) instead of 4-chloro-3-fluoro-pyrazolo[1,5-a]pyridine-7-carbonitrile (compound E1). Intermediate F (166 mg) was obtained as a white solid. MS: calc'd 405 (MH+), measured 405 (MH+).

Intermediate L

[(2R,6R)-4-(8-cyano-2-deuterio-5-quinolyl)-6-methyl-morpholin-2-yl]methyl trifluoromethane-sulfonate

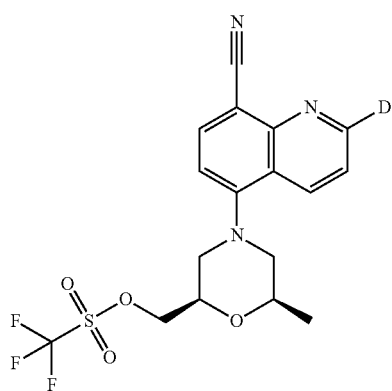 [SMILES: [2H]c1ccc2c(N3C[C@H](COS(=O)(=O)C(F)(F)F)O[C@H](C)C3)ccc(C#N)c2n1]

The intermediate L was prepared according to the following scheme:

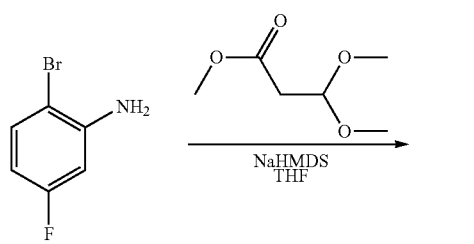

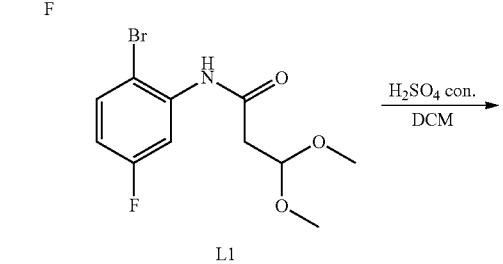

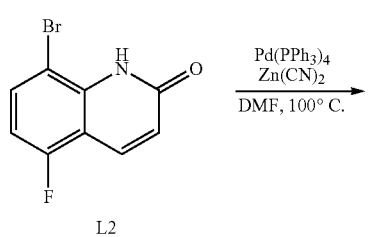

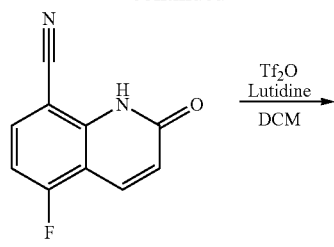

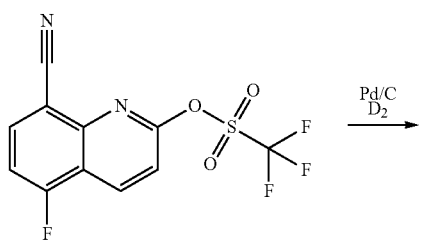

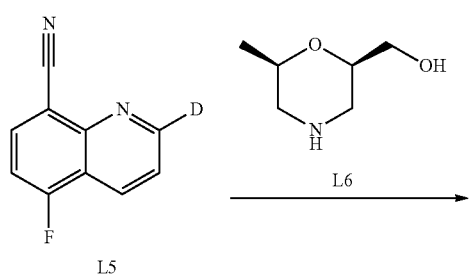

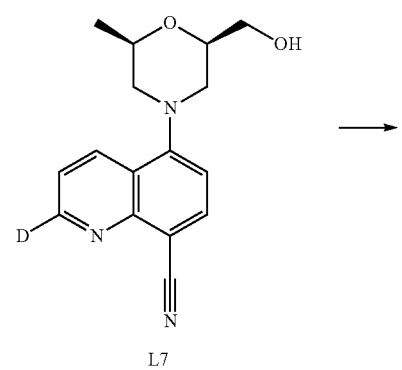

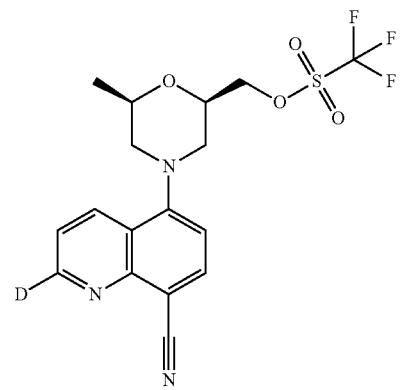

Step 1: Preparation of N-(2-bromo-5-fluoro-phenyl)-3,3-dimethoxy-propanamide (Compound L1)

To the solution of 2-bromo-5-fluoroaniline (CAS: 1003-99-2, Vendor: TCI, 50 g, 263.14 mmol) and methyl 3,3-dimethoxypropionate (CAS: 7424-91-1, Vendor: Accela, 45 mL, 315.77 mmol) in THF (150 mL) was added NaHMDS in THF (1M, 394 mL, 394.72 mmol) dropwise at 0° C. After being stirred at 0° C. for 10 mins, the mixture was warmed up to 15° C. and stirred for 18 hrs. The reaction was quenched by addition of 100 mL sat. NH$_4$Cl and concentrated to about 300 mL. The solution was diluted with 500 mL water and extracted with 200 mL EA for three times. The combined organic layer was washed with 200 mL water twice and 100 mL brine, dried over Na$_2$SO$_4$ and concentrated to give the crude product L1 (100 g) as a brown oil. MS calc'd 321 (MH$^+$), measured 321 (MH$^+$).

Step 2: Preparation of 8-bromo-5-fluoro-1H-quinolin-2-one (Compound L2)

A solution of N-(2-bromo-5-fluoro-phenyl)-3,3-dimethoxy-propanamide (compound L1, 100 g, 238.46 mmol) in DCM (500 mL) was added to concentrated sulfuric acid (300 mL) at 0° C. After being stirred at 15° C. for 2 hrs, the mixture was poured slowly into 2000 mL ice-water, a yellow precipitate was appeared. The mixture was filtered, and the wet-cake was washed with 500 mL water, 200 mL isopropyl alcohol and 300 mL PE. The solid was dried in vacuum to give compound L2 (50 g) as a yellow solid. MS calc'd 242 (MH$^+$), measured 242 (MH$^+$).

Step 3: Preparation of 5-fluoro-2-oxo-1H-quinoline-8-carbonitrile (Compound L3)

A solution of 8-bromo-5-fluoro-1H-quinolin-2-one (compound L2, 50 g, 206.58 mmol), zinc cyanide (48.50 g, 413.15 mmol), Pd(PPh$_3$)$_4$ (24.29 g, 21.02 mmol) in DMF (1000 mL) was stirred at 120° C. for 5 hrs. After being cooled down, the reaction mixture was quenched with 300 mL saturated NH$_4$Cl, diluted with 2000 mL water and extracted with 500 mL DCM for three times. The combined organic layer was washed with 500 mL water twice and 200 mL brine once, dried over Na$_2$SO$_4$ and concentrated to give the crude product which was purified by silica gel chromatography (PE/EA=3/1) to give compound L3 (29 g) as a yellow solid. MS calc'd 189 (MH$^+$), measured 189 (MH$^+$).

Step 4: Preparation of (8-cyano-5-fluoro-2-quinolyl) trifluoromethanesulfonate (Compound L4)

To the solution of 5-fluoro-2-oxo-1H-quinoline-8-carbonitrile (compound L3, 17 g, 90.35 mmol), 2,6-dimethylpyridine (38.7 g, 361 mmol) in DCM (500 mL) was added trifluoromethanesulfonic anhydride (51 g, 181 mmol) at 0° C. After being stirred at 0° C. for 1 h, the mixture was diluted with 500 mL water and extracted with 200 mL DCM for three times. The combined organic layer was washed with 200 mL water twice and 100 mL brine once, dried over Na$_2$SO$_4$ and concentrated to give the crude product which was purified by silica gel chromatography (PE/EA=5/1) to give compound L4 (23 g) as a yellow solid. MS calc'd 321 (MH$^+$), measured 321 (MH$^+$).

Step 5: Preparation of 2-deuterio-5-fluoro-quinoline-8-carbonitrile (Compound L5)

To the solution of (8-cyano-5-fluoro-2-quinolyl) trifluoromethanesulfonate (compound L4, 23 g, 71.83 mmol) in THF (230 mL) and deuterium oxide (100 mL) was added potassium carbonate (19.8 g, 1.44 mol) and Pd/C (10 wt. %, 6 g). The mixture was stirred at 40° C. for 5 hrs under deuterium atmosphere. Then the mixture was filtered and the filtrate was concentrated and purified by silica gel chromatography (PE/EA=5/1) to give compound L5 (11.4 g) as a light yellow solid. MS calc'd 174 (MH$^+$), measured 174 (MH$^+$).

Step 6: Preparation of 5-((2R,6R)-2-(hydroxymethyl)-6-methylmorpholino)quinoline-8-carbonitrile-2-d (Compound L7)

A mixture of 5-fluoroquinoline-8-carbonitrile-2-d (compound L5, 611 mg, 3.53 mmol), ((2R,6R)-6-methylmorpholin-2-yl)methanol hydrochloride salt (compound L6, 710 mg, 4.23 mmol), N-ethyl-N-isopropylpropan-2-amine (1.37 g, 10.6 mmol) in DMSO (3 mL) was stirred at 120° C. for 16 hours. Then the solution was diluted with EA and washed with water and brine. The organic layer was dried and concentrated. The residue was purified by silica gel chromatography (EA/PE from 20% to 80%) to afford 5-((2R,6R)-2-(hydroxymethyl)-6-methylmorpholino)quinoline-8-carbonitrile-2-d (compound L7, 990 mg) as a yellow solid. MS: calc'd 285 (MH$^+$), measured 285 (MH$^+$).

Step 7: Preparation of ((2R,6R)-4-(8-cyanoquinolin-5-yl-2-d)-6-methylmorpholin-2-yl)methyl trifluoromethanesulfonate (Intermediate L)

To a solution of 5-((2R,6R)-2-(hydroxymethyl)-6-methylmorpholino) quinoline-8-carbonitrile-2-d (compound L7, 3 g) and 2,6-dimethylpyridine (3.39 g, 3.77 ml, 31.7 mmol) in CH$_2$Cl$_2$ (20 ml) was added trifluoromethanesulfonic anhydride (4.47 g, 2.67 ml, 15.8 mmol) dropwise at 0° C. The mixture was stirred at 0° C. for 1 h, then diluted with DCM and washed with saturated NH$_4$Cl solution and brine. The organic layer was dried over Na$_2$SO$_4$ and concentrated. The residue was purified by silica gel chromatography (EA/PE from 20% to 60%) to afford ((2R,6R)-4-(8-cyano-quinolin-5-yl-2-d)-6-methylmorpholin-2-yl)methyl trifluoromethanesulfonate (Intermediate L 4.087 g) as a yellow solid. MS: calc'd 417 (MH$^+$), measured 417 (MH$^+$).

Intermediate M

[(2R,6R)-6-methyl-4-(1-methyl-2-oxo-1,8-naphthyridin-4-yl)morpholin-2-yl]methyl trifluoromethanesulfonate

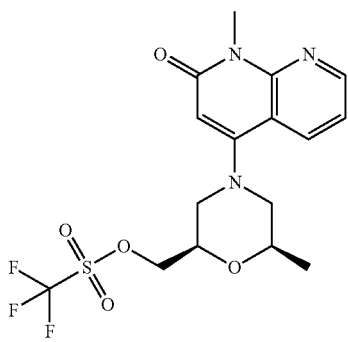 [SMILES: C[C@@H]1CN(c2cc(=O)n(C)c3ncccc23)C[C@H](COS(=O)(=O)C(F)(F)F)O1]

The title compound was prepared in analogy to the preparation of Intermediate A by using 4-bromo-1-methyl-1,8-naphthyridin-2-one (compound M1) instead of 5-bromoquinoline-8-carbonitrile (compound A2). Intermediate M (140 mg) was obtained as a yellow solid. MS: calc'd 422 (MH$^+$), measured 422 (MH$^+$).

The compound M1 was prepared according to the following scheme:

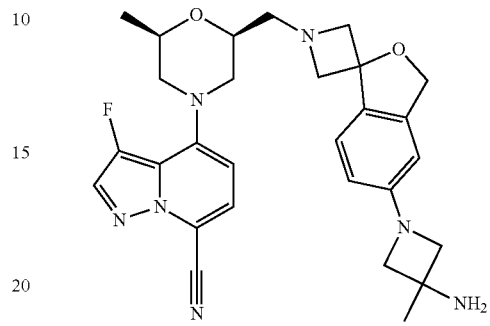

Preparation of
4-bromo-1-methyl-1,8-naphthyridin-2-one
(Compound M1)

To the solution of 4-bromo-1,8-naphthyridin-2(1H)-one (CAS: 72235-36-0, Vendor: Accela, 370 mg, 1.64 mmol) in DMF (15 mL) was added iodomethane (2.33 g, 16.40 mmol) and Cs$_2$CO$_3$ (1.07 g, 3.29 mmol). The reaction mixture was stirred at 80° C. overnight. After being cooled down, the reaction was quenched by ice-water (30 mL). The solid was collected by filtration to give crude compound M1 (419 mg) which was used directly for next step. MS calc'd 239 (MH$^+$), measured 239 (MH$^+$). $^1$H NMR (400 MHz, METHANOL-d$_4$) δ=8.72 (dd, J=1.7, 4.7 Hz, 1H), 8.39 (dd, J=1.7, 7.9 Hz, 1H), 7.43 (dd, J=4.7, 8.0 Hz, 1H), 7.20 (s, 1H), 3.83 (s, 3H).

Example 1

4-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile

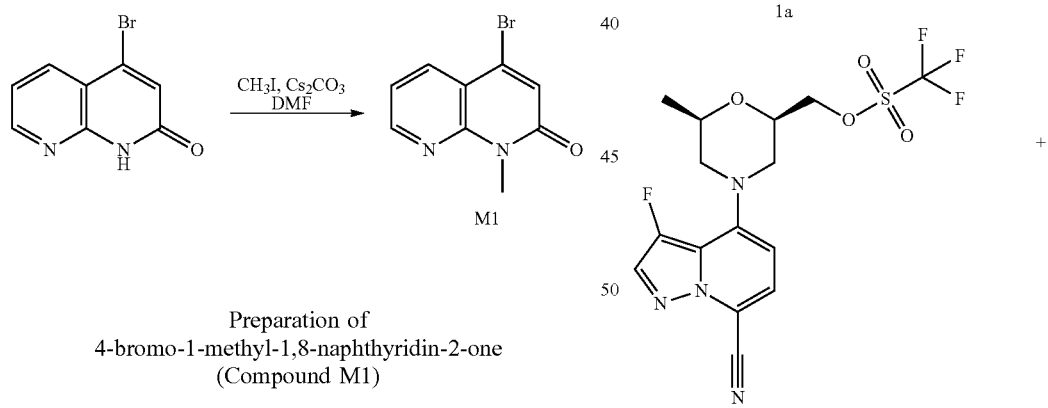

The title compound was prepared according to the following scheme:

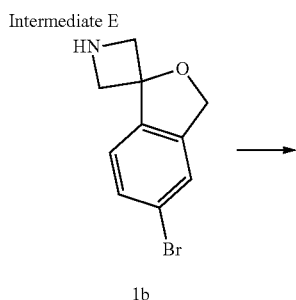

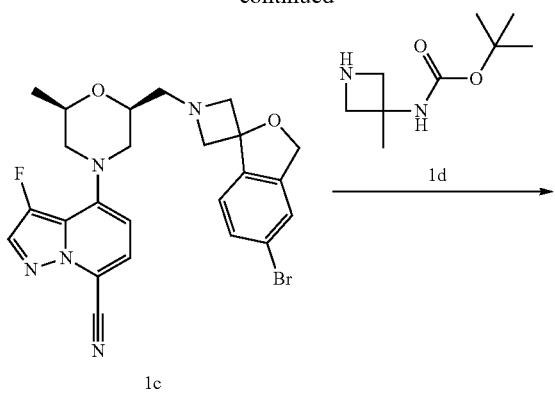

1c

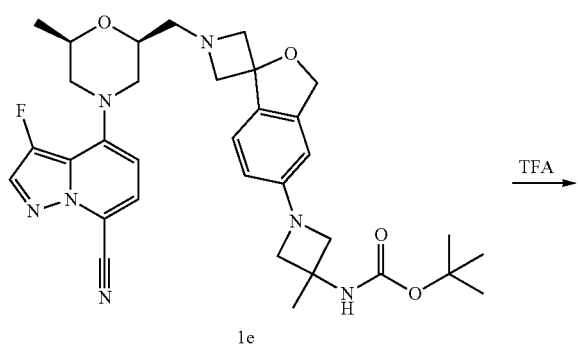

1e

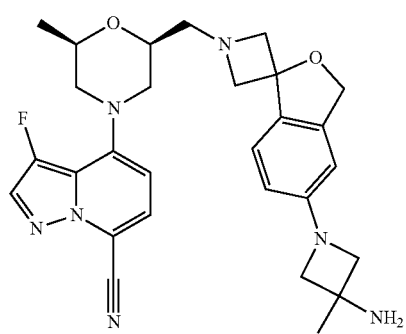

1

Step 1: 6-bromospiro[1H-isobenzofuran-3,3'-azetidine] (Compound 1b)

To a solution of tert-butyl 6-bromospiro[1H-isobenzofuran-3,3'-azetidine]-1'-carboxylate (compound 1a, CAS: 1398609-80-7, Pharmablock, 260 mg) in DCM (2 mL) was added trifluoroacetic acid (0.5 mL). After being stirred at rt for 3 hrs, the mixture was concentrated in vacuo to give a white oil which can be used without purification. 184 mg of 6-bromospiro[1H-isobenzofuran-3,3'-azetidine] (compound 1b) was obtained. MS calc'd 242 (MH$^+$), measured 242 (MH$^+$).

Step 2: 4-[(2S,6R)-2-[(6-bromospiro[1H-isobenzofuran-3,3'-azetidine]-1'-yl)methyl]-6-methyl-morpholin-4-yl]-3-fluoro-pyrazolo[1,5-a]pyridine-7-carbonitrile (Compound 1c)

A solution of 6-bromospiro[1H-isobenzofuran-3,3'-azetidine] (compound 1b, 35 mg, 146 µmol) and [(2R,6R)-4-(7-cyano-3-fluoro-pyrazolo[1,5-a]pyridin-4-yl)-6-methyl-morpholin-2-yl]methyl trifluoromethanesulfonate (Intermediate E, 62 mg, 146 µmol) and DIPEA (0.2 mL) in CH$_2$Cl$_2$ (20 mL) was stirred at room temperature for 2 hrs. The mixture was then diluted with DCM and washed with brine. The organic layer was dried over Na$_2$SO$_4$ and concentrated. The residue was purified by silica gel chromatography (EA/PE from 0% to 100%) to get 4-[(2S,6R)-2-[(6-bromospiro[1H-isobenzofuran-3,3'-azetidine]-1'-yl)methyl]-6-methyl-morpholin-4-yl]-3-fluoro-pyrazolo[1,5-a]pyridine-7-carbonitrile (compound 1c, 52 mg) as a yellow solid. MS: calc'd 513 (MH$^+$), measured 513 (MH$^+$).

Step 3: tert-butyl N-[1-[1'-[[(2S,6R)-4-(7-cyano-3-fluoro-pyrazolo[1,5-a]pyridin-4-yl)-6-methyl-morpholin-2-yl]methyl]spiro[3H-isobenzofuran-1,3'-azetidine]-5-yl]-3-methyl-azetidin-3-yl]carbamate (Compound 1e)

To a solution of 4-[(2S,6R)-2-[(6-bromospiro[1H-isobenzofuran-3,3'-azetidine]-1'-yl)methyl]-6-methyl-morpholin-4-yl]-3-fluoro-pyrazolo[1,5-a]pyridine-7-carbonitrile (compound 1c, 74 mg, 144 µmol) in dioxane (10 mL) was added RuPhos-Pd-G2 (11 mg, 14.4 µmol), tert-butyl (3-methylazetidin-3-yl)carbamate (compound 1d, 40 mg, 217 µmol) and K$_2$CO$_3$ (100 mg, 722 µmol). The reaction mixture was stirred at 90° C. under N$_2$ overnight. Then the mixture was filtered and the filtrate was concentrated under reduced pressure to afford crude product which can be used in next step without purification (compound 1e, 89 mg). MS: calc'd 618 (MH$^+$), measured 618 (MH$^+$).

Step 4: 4-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile (Example 1)

To a solution of tert-butyl N-[1-[1'-[[(2S,6R)-4-(7-cyano-3-fluoro-pyrazolo[1,5-a]pyridin-4-yl)-6-methyl-morpholin-2-yl]methyl]spiro[3H-isobenzofuran-1,3'-azetidine]-5-yl]-3-methyl-azetidin-3-yl]carbamate (compound 1e, 89 mg) in DCM (10 mL) was added TFA (2 mL) at 0° C. The reaction mixture was stirred at r.t. for 2 hrs. Then the mixture was concentrated to crude product, which was purified by prep-HPLC to afford Example 1 (7 mg) as a yellow solid. MS calc'd 518 (MH$^+$), measured 518 (MH$^+$). $^1$H NMR (METHANOL-d$_4$, 400 MHz) δ 7.91 (d, J=3.7 Hz, 1H), 7.46 (d, J=8.3 Hz, 1H), 7.35 (d, J=7.9 Hz, 1H), 6.42-6.56 (m, 2H), 6.29-6.39 (m, 1H), 5.00 (s, 2H), 4.35-4.57 (m, 3H), 3.98-4.13 (m, 2H), 3.76-3.95 (m, 5H), 3.36-3.61 (m, 4H), 2.49-2.80 (m, 2H), 1.57 (s, 3H), 1.18 ppm (d, J=6.2 Hz, 3H).

Example 2

3-fluoro-4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile

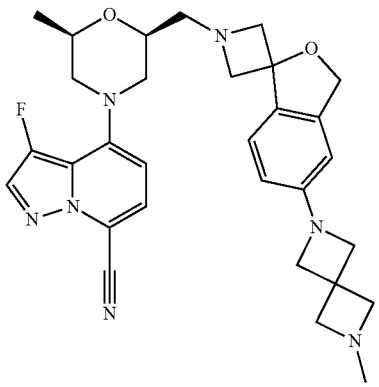 [SMILES: C[C@@H]1CN(c2ccc(C#N)n3ncc(F)c23)C[C@H](CN2CC3(C2)OCc2cc(N4CC5(CN(C)C5)C4)ccc23)O1]

The title compound was prepared in analogy to the preparation of Example 1 by using 2-methyl-2,6-diazaspiro[3.3]heptane instead of tert-butyl (3-methylazetidin-3-yl)carbamate (compound 1d). Example 2 (26 mg) was obtained as a yellow solid. MS: calc'd 544 (MH⁺), measured 544 (MH⁺). ¹H NMR (METHANOL-d₄, 400 MHz) δ 8.01 (d, J=3.7 Hz, 1H), 7.53 (d J=8.2 Hz, 1H), 7.44 (d, J=7.9 Hz, 1H), 6.55 (d, J=7.9 Hz, 2H), 6.39 (d, J=1.1 Hz, 1H), 5.08 (s, 2H), 4.53 (br d, J=11.5 Hz, 5H), 4.25 (br d, J=11.1 Hz, 2H), 4.0-4.2 (m, 6H), 3.9-4.0 (m, 1H), 3.5-3.7 (m, 4H), 2.94 (s, 3H), 2.7-2.8 (m, 1H), 2.6-2.7 (m, 1H), 1.28 (d, J=6.2 Hz, 3H).

Example 3

3-fluoro-4-[(2S,6R)-2-[[6-[[(3S,4R)-4-fluoropyrrolidin-3-yl]amino]spiro[1H-isobenzofuran-3,3'-azetidine]-1'-yl]methyl]-6-methyl-morpholin-4-yl]pyrazolo[1,5-a]pyridine-7-carbonitrile

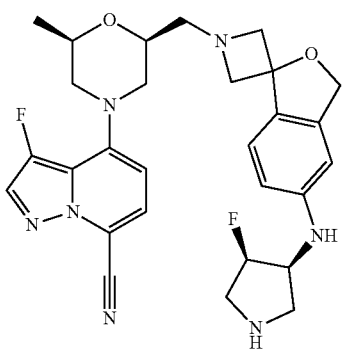 [SMILES: C[C@@H]1CN(c2ccc(C#N)n3ncc(F)c23)C[C@H](CN2CC3(C2)OCc2cc(N[C@H]4CNC[C@H]4F)ccc23)O1]

The title compound was prepared in analogy to the preparation of Example 1 by using tert-butyl (3S,4R)-3-amino-4-fluoropyrrolidine-1-carboxylate (CAS: 1174020-30-4, vendor: PharmaBlock) instead of tert-butyl (3-methylazetidin-3-yl)carbamate (compound 1d). Example 3 (19 mg) was obtained as a light brown solid. MS: calc'd 536 (MH⁺), measured 536 (MH⁺). ¹H NMR (METHANOL-d₄, 400 MHz) δ 8.00 (d, J=3.5 Hz, 1H), 7.51 (br d, J=8.3 Hz, 1H), 7.44 (d, J=7.9 Hz, 1H), 6.85 (br d, J=8.4 Hz, 1H), 6.68 (s, 1H), 6.55 (d, J=7.9 Hz, 1H), 5.2-5.4 (m, 1H), 5.08 (s, 2H), 4.4-4.6 (m, 4H), 4.1-4.2 (m, 1H), 3.9-4.0 (m, 1H), 3.7-3.8 (m, 2H), 3.59 (br d, J=12.7 Hz, 6H), 3.21 (br t, J=11.2 Hz, 1H), 2.79 (br t, J=11.2 Hz, 1H), 2.68 (br t, J=11.3 Hz, 1H), 1.28 (d, J=6.2 Hz, 3H).

Example 4

3-fluoro-4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile

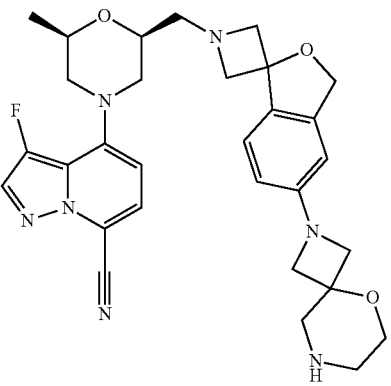 [SMILES: C[C@@H]1CN(c2ccc(C#N)n3ncc(F)c23)C[C@H](CN2CC3(C2)OCc2cc(N4CC5(CNCCO5)C4)ccc23)O1]

The title compound was prepared in analogy to the preparation of Example 1 by using tert-butyl 2-oxa-5,8-diazaspiro[3.5]nonane-8-carboxylate (CAS: 1367777-12-5, vendor: PharmaBlock) instead of tert-butyl (3-methylazetidin-3-yl)carbamate (compound 1d). Example 4 (33 mg) was obtained as a light brown solid. MS: calc'd 560 (MH⁺), measured 560 (MH⁺). ¹H NMR (METHANOL-d₄, 400 MHz) δ 8.01 (d, J=3.7 Hz, 1H), 7.54 (d, J=8.3 Hz, 1H), 7.44 (d, J=7.8 Hz, 1H), 6.59 (br d, J=8.6 Hz, 1H), 6.55 (d, J=7.9 Hz, 1H), 6.44 (d, J=1.3 Hz, 1H), 5.10 (s, 2H), 4.6-4.8 (m, 1H), 4.4-4.6 (m, 3H), 4.1-4.2 (m, 1H), 4.0-4.1 (m, 2H), 3.9-4.0 (m, 3H), 3.8-3.8 (m, 2H), 3.5-3.7 (m, 4H), 3.5-3.5 (m, 2H), 3.2-3.3 (m, 2H), 2.6-2.8 (m, 2H), 1.28 (d, J=6.2 Hz, 3H).

Example 5

4-[(2S,6R)-2-[[6-[(3S)-3-amino-3-methyl-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile

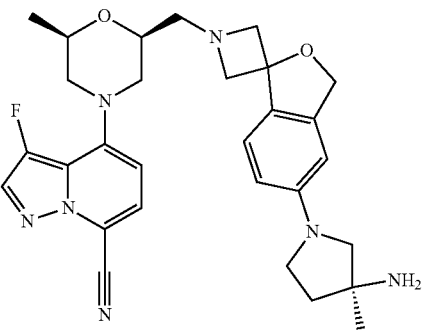 [SMILES: C[C@@H]1CN(c2ccc(C#N)n3ncc(F)c23)C[C@H](CN2CC3(C2)OCc2cc(N4CC[C@](C)(N)C4)ccc23)O1]

The title compound was prepared in analogy to the preparation of Example 1 by using (S)-tert-Butyl (3-methylpyrrolidin-3-yl)carbamate (CAS: 927652-04-8, vendor: PharmaBlock) instead of tert-butyl (3-methylazetidin-3-yl)carbamate (compound 1d). Example 5 (13 mg) was obtained as a white solid. MS: calc'd 532 (MH+), measured 532 (MH+). ¹H NMR (METHANOL-d₄, 400 MHz) δ 7.89 (d, J=3.7 Hz, 1H), 7.32 (dd, J=3.4, 8.1 Hz, 2H), 6.46 (dd, J=1.9, 8.4 Hz, 1H), 6.41 (d, J=7.9 Hz, 1H), 6.27 (s, 1H), 4.88 (s, 2H), 3.7-3.8 (m, 2H), 3.5-3.6 (m, 5H), 3.4-3.4 (m, 2H), 3.2-3.3 (m, 1H), 3.09 (s, 2H), 2.5-2.7 (m, 4H), 1.8-1.9 (m, 2H), 1.25 (s, 3H), 1.13 (d, J=6.4 Hz, 3H).

Example 6

3-fluoro-4-[(2R,6S)-2-methyl-6-[(6-piperazin-1-ylspiro[1H-isobenzofuran-3,3'-azetidine]-1'-yl)methyl]morpholin-4-yl]pyrazolo[1,5-a]pyridine-7-carbonitrile

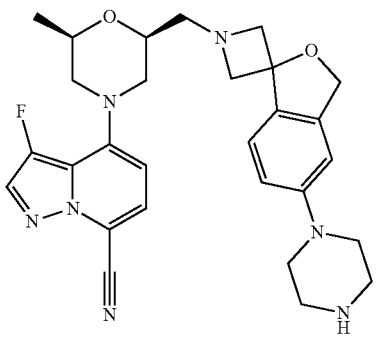 [SMILES: C[C@@H]1CN(c2ccc(C#N)n3ncc(F)c23)C[C@H](CN2CC3(C2)OCc2cc(N4CCNCC4)ccc23)O1]

The title compound was prepared in analogy to the preparation of Example 1 by using tert-butyl piperazine-1-carboxylate instead of tert-butyl (3-methylazetidin-3-yl)carbamate (compound 1d). Example 6 (33 mg) was obtained as a yellow solid. MS: calc'd 518 (MH+), measured 518 (MH+). ¹H NMR (METHANOL-d₄, 400 MHz) δ 8.01 (d, J=3.5 Hz, 1H), 7.63 (d, J=8.4 Hz, 1H), 7.44 (d, J=7.9 Hz, 1H), 7.12 (dd, J=2.1, 8.5 Hz, 1H), 6.9-7.0 (m, 1H), 6.55 (d, J=7.9 Hz, 1H), 5.13 (s, 2H), 4.5-4.5 (m, 2H), 4.1-4.2 (m, 1H), 3.9-4.0 (m, 1H), 3.5-3.6 (m, 4H), 3.4-3.5 (m, 5H), 3.4-3.4 (m, 5H), 2.78 (t, J=11.2 Hz, 1H), 2.6-2.7 (m, 1H), 1.28 (d, J=6.2 Hz, 3H).

Example 7

4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile

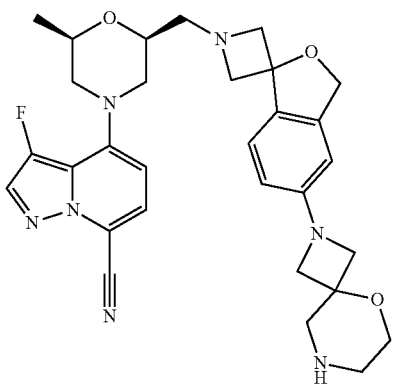 [SMILES: C[C@@H]1CN(c2ccc(C#N)n3ncc(F)c23)C[C@H](CN2CC3(C2)OCc2cc(N4CC5(CNCCO5)C4)ccc23)O1]

The title compound was prepared in analogy to the preparation of Example 1 by using [(2R,6R)-4-(7-cyanopyrazolo[1,5-a]pyridin-4-yl)-6-methyl-morpholin-2-yl]methyl trifluoromethanesulfonate (Intermediate F) and tert-butyl 2-oxa-5,8-diazaspiro[3.5]nonane-8-carboxylate (CAS: 1367777-12-5, vendor: PharmaBlock) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl (3-methylazetidin-3-yl)carbamate (compound 1d). Example 7 (7 mg) was obtained as a white solid. MS: calc'd 542 (MH+), measured 542 (MH+). ¹H NMR (METHANOL-d₄, 400 MHz) δ 7.93 (d, J=2.3 Hz, 1H), 7.4-7.4 (m, 1H), 7.36 (s, 1H), 6.77 (d, J=2.4 Hz, 1H), 6.50 (d, J=8.1 Hz, 1H), 6.43 (dd, J=1.8, 8.2 Hz, 1H), 6.27 (s, 1H), 4.89 (s, 2H), 4.49 (br s, 2H), 3.8-3.8 (m, 4H), 3.6-3.6 (m, 6H), 3.5-3.6 (m, 2H), 2.93 (s, 2H), 2.7-2.7 (m, 4H), 2.5-2.6 (m, 2H), 1.15 (d, J=6.2 Hz, 3H).

Example 8

4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile

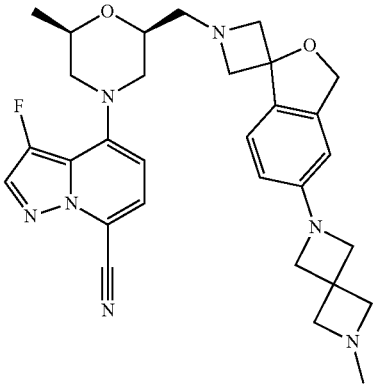 [SMILES: C[C@@H]1CN(c2ccc(C#N)n3ncc(F)c23)C[C@H](CN2CC3(C2)OCc2cc(N4CC5(CN(C)C5)C4)ccc23)O1]

The title compound was prepared in analogy to the preparation of Example 1 by using [(2R,6R)-4-(7-cyanopyrazolo[1,5-a]pyridin-4-yl)-6-methyl-morpholin-2-yl]methyl trifluoromethanesulfonate (Intermediate F) and 2-methyl-2,6-diazaspiro[3.3]heptane instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl (3-methylazetidin-3-yl)carbamate (compound 1d). Example 8 (25 mg) was obtained as a white solid. MS: calc'd 526 (MH+), measured 526 (MH+). ¹H NMR (METHANOL-d4, 400 MHz) δ 8.02 (d, J=2.3 Hz, 1H), 7.47 (d, J=4.9 Hz, 1H), 7.45 (d, J=5.1 Hz, 1H), 6.86 (d, J=2.4 Hz, 1H), 6.59 (d, J=7.9 Hz, 1H), 6.48 (dd, J=2.0, 8.3 Hz, 1H), 6.33 (d, J=1.3 Hz, 1H), 4.97 (s, 2H), 3.8-3.9 (m, 7H), 3.73 (br d, J=12.1 Hz, 1H), 3.6-3.7 (m, 4H), 3.48 (s, 4H), 2.7-2.8 (m, 3H), 2.6-2.7 (m, 1H), 2.36 (s, 3H), 1.24 (d, J=6.2 Hz, 3H).

Example 9

4-[(2S,6R)-2-[[6-(3-aminoazetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile

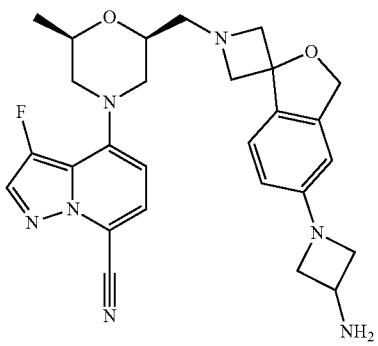 [SMILES: C[C@@H]1CN(c2ccc(C#N)n3ncc(F)c23)C[C@H](CN2CC3(C2)OCc2cc(N4CC(N)C4)ccc23)O1]

The title compound was prepared in analogy to the preparation of Example 1 by tert-Butyl azetidin-3-ylcarbamate (CAS: 91188-13-5, vendor: BePharm) instead of tert-butyl (3-methylazetidin-3-yl)carbamate (compound 1d). Example 9 (7 mg) was obtained as a white solid. MS: calc'd 504 (MH$^+$), measured 504 (MH$^+$). $^1$H NMR (METHANOL-d4, 400 MHz) δ 8.01 (d, J=3.7 Hz, 1H), 7.55 (d, J=8.3 Hz, 1H), 7.45 (d, J=7.8 Hz, 1H), 6.5-6.6 (m, 2H), 6.44 (s, 1H), 5.10 (s, 2H), 4.1-4.3 (m, 4H), 3.9-4.0 (m, 3H), 3.7-3.8 (m, 1H), 3.5-3.7 (m, 4H), 3.4-3.5 (m, 1H), 2.6-2.8 (m, 2H), 2.03 (s, 2H), 1.28 (d, J=6.2 Hz, 3H).

Example 10

4-[(2S,6R)-2-[[6-[(3S,4S)-3-amino-4-hydroxy-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile

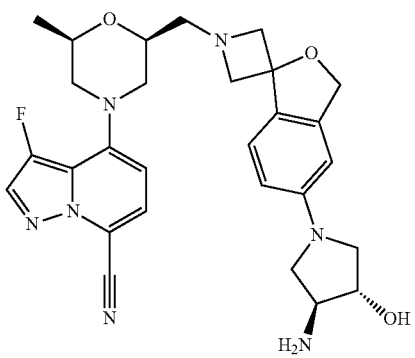 [SMILES: C[C@@H]1CN(c2ccc(C#N)n3ncc(F)c23)C[C@H](CN2CC3(C2)OCc2cc(N4C[C@H](N)[C@@H](O)C4)ccc23)O1]

The title compound was prepared in analogy to the preparation of Example 1 by tert-Butyl ((3R,4R)-4-hydroxy-pyrrolidin-3-yl)carbamate hydrochloride (CAS: 1820575-70-9, vendor: BePharm) instead of tert-butyl (3-methylazetidin-3-yl)carbamate (compound 1d). Example 10 (8 mg) was obtained as a light yellow solid. MS: calc'd 534 (MH$^+$), measured 534 (MH$^+$). $^1$H NMR (METHANOL-d$_4$, 400 MHz) δ 8.01 (d, J=3.5 Hz, 1H), 7.5-7.6 (m, 1H), 7.44 (d, J=7.9 Hz, 1H), 6.7-6.8 (m, 1H), 6.5-6.6 (m, 2H), 5.11 (br d, J=9.2 Hz, 2H), 4.4-4.6 (m, 4H), 4.38 (d, J=3.8 Hz, 1H), 4.1-4.2 (m, 2H), 3.9-4.0 (m, 2H), 3.7-3.8 (m, 2H), 3.5-3.7 (m, 4H), 3.4-3.5 (m, 2H), 2.7-2.8 (m, 2H), 1.28 (d, J=6.2 Hz, 3H).

Example 11

5-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-2-deuterio-quinoline-8-carbonitrile

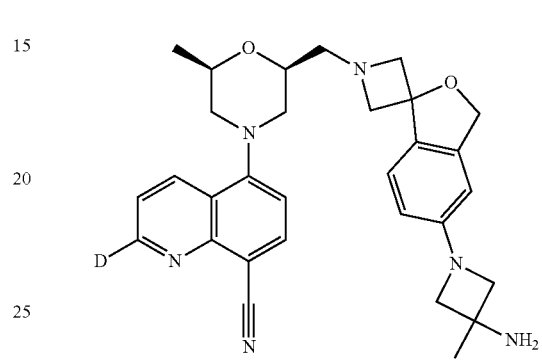

The title compound was prepared in analogy to the preparation of Example 1 by using [(2R,6R)-4-(8-cyano-2-deuterio-5-quinolyl)-6-methyl-morpholin-2-yl]methyl trifluoromethanesulfonate (Intermediate L) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 11 (13 mg) was obtained as a yellow solid. MS: calc'd 512 (MH$^+$), measured 512 (MH$^+$). $^1$H NMR (400 MHz, METHANOL-d4) δ 8.66 (d, J=8.7 Hz, 1H), 8.17 (d, J=8.1 Hz, 1H), 7.65 (d, J=8.7 Hz, 1H), 7.55 (d, J=8.3 Hz, 1H), 7.28 (d, J=8.1 Hz, 1H), 6.59 (dd, J=8.3, 2.0 Hz, 1H), 6.44 (s, 1H), 5.08 (s, 2H), 4.21-4.68 (m, 5H), 4.07-4.18 (m, 1H), 3.86-4.01 (m, 4H), 3.37-3.58 (m, 4H), 2.64-2.91 (m, 2H), 1.67 (s, 3H), 1.28 (d, J=6.2 Hz, 3H).

Example 12

4-[(2S,6R)-2-[[6-(2,6-diazaspiro[3.3]heptan-2-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile

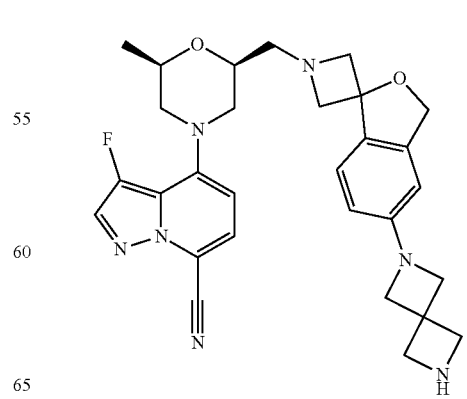

The title compound was prepared in analogy to the preparation of Example 1 by tert-Butyl 2,6-diazaspiro[3.3]heptane-2-carboxylate oxalate (CAS: 1041026-71-4, vendor: PharmaBlock) instead of tert-butyl (3-methylazetidin-3-yl)carbamate (compound 1d). Example 12 (18 mg) was obtained as a light brown solid. MS: calc'd 530 (MH⁺), measured 530 (MH⁺). ¹H NMR (METHANOL-d4, 400 MHz) δ 8.01 (d, J=3.5 Hz, 1H), 7.52 (d, J=8.3 Hz, 1H), 7.44 (d, J=7.8 Hz, 1H), 6.55 (d, J=7.9 Hz, 2H), 6.39 (d, J=1.3 Hz, 1H), 5.08 (s, 2H), 4.4-4.6 (m, 4H), 4.30 (s, 4H), 4.1-4.2 (m, 1H), 4.06 (s, 4H), 3.9-4.0 (m, 1H), 3.5-3.6 (m, 4H), 2.78 (t, J=11.2 Hz, 1H), 2.6-2.7 (m, 1H), 1.28 (d, J=6.2 Hz, 3H).

Example 13

4-[(2S,6R)-2-[[6-(3-aminoazetidin-1-yl)spiro[1H-isobenzofuran-3,3'-azetidine]-1'-yl]methyl]-6-methyl-morpholin-4-yl]-1-methyl-1,8-naphthyridin-2-one

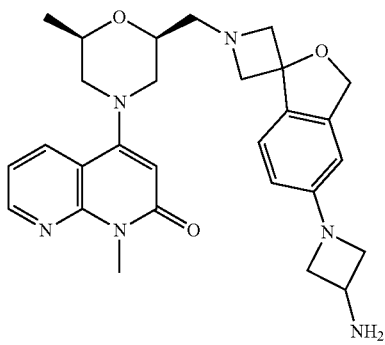 [SMILES: C[C@@H]1CN(c2cc(=O)n(C)c3ncccc23)C[C@H](CN2CC3(C2)OCc2cc(N4CC(N)C4)ccc23)O1]

The title compound was prepared in analogy to the preparation of Example 1 by using tert-butyl N-(azetidin-3-yl)carbamate and [(2R,6R)-6-methyl-4-(1-methyl-2-oxo-1,8-naphthyridin-4-yl)morpholin-2-yl]methyl trifluoromethanesulfonate (Intermediate M) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 13 (4 mg) was obtained as a yellow solid. MS: calc'd 503 (MH⁺), measured 503 (MH⁺). ¹H NMR (400 MHz, METHANOL-d4) δ 8.64 (dd, J=4.6, 1.8 Hz, 1H), 8.25 (dd, J=8.0, 1.8 Hz, 1H), 7.43 (d, J=8.3 Hz, 1H), 7.30 (dd, J=8.0, 4.6 Hz, 1H), 6.48 (dd, J=8.3, 2.0 Hz, 1H), 6.33 (d, J=0.9 Hz, 1H), 6.15 (s, 1H), 4.96 (s, 2H), 4.12 (t, J=7.3 Hz, 2H), 3.80-4.00 (m, 3H), 3.72 (d, J=2.9 Hz, 3H), 3.45-3.51 (m, 3H), 3.11-3.23 (m, 5H), 2.48-2.82 (m, 4H), 1.22 (d, J=6.2 Hz, 3H).

Example 14

5-[(2S,6R)-2-[[6-(3-aminoazetidin-1-yl)spiro[1H-isobenzofuran-3,3'-azetidine]-1'-yl]methyl]-6-methyl-morpholin-4-yl]-2-deuterio-quinoline-8-carbonitrile

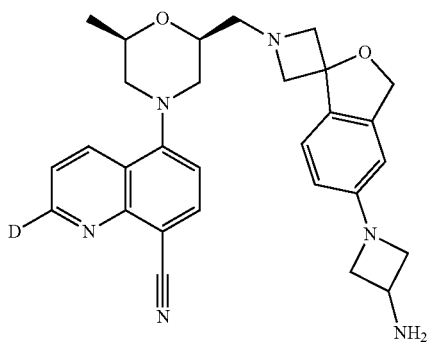 [SMILES: [2H]c1ccc2c(N3C[C@H](CN4CC5(C4)OCc4cc(N6CC(N)C6)ccc45)O[C@H](C)C3)ccc(C#N)c2n1]

The title compound was prepared in analogy to the preparation of Example 1 by using tert-butyl N-(azetidin-3-yl)carbamate and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 14 (19 mg) was obtained as a yellow solid. MS: calc'd 498 (MH⁺), measured 498 (MH⁺). ¹H NMR (400 MHz, METHANOL-d4) δ 8.66 (d, J=8.6 Hz, 1H), 8.17 (d, J=7.9 Hz, 1H), 7.65 (d, J=8.6 Hz, 1H), 7.56 (br d, J=8.2 Hz, 1H), 7.29 (d, J=8.1 Hz, 1H), 6.59 (br d, J=8.1 Hz, 1H), 6.45 (d, J=1.5 Hz, 1H), 5.11 (s, 2H), 4.43-4.70 (m, 3H), 4.08 (m, 5H), 3.84-3.99 (m, 2H), 3.38-3.72 (m, 5H), 2.62-2.91 (m, 2H), 1.29 (d, J=6.2 Hz, 3H).

Example 15

2-deuterio-5-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]quinoline-8-carbonitrile

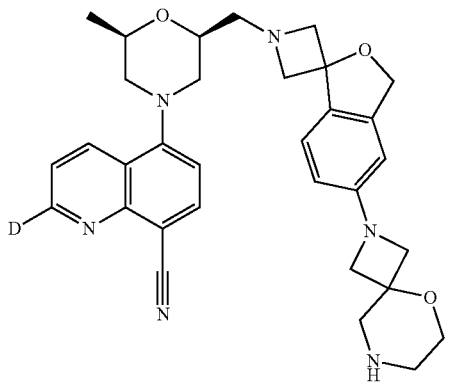 [SMILES: [2H]c1ccc2c(N3C[C@H](CN4CC5(C4)OCc4cc(N6CC7(CNCCO7)C6)ccc45)O[C@H](C)C3)ccc(C#N)c2n1]

The title compound was prepared in analogy to the preparation of Example 1 by using tert-butyl 5-oxa-2,8- diazaspiro[3.5]nonane-8-carboxylate and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 15 (9 mg) was obtained as a yellow solid. MS: calc'd 554 (MH+), measured 554 (MH+). $^1$H NMR (400 MHz, METHANOL-d4) δ 8.55 (d, J=8.7 Hz, 1H), 8.05 (d, J=8.1 Hz, 1H), 7.53 (d, J=8.7 Hz, 1H), 7.36 (d, J=8.2 Hz, 1H), 7.15 (d, J=8.1 Hz, 1H), 6.42 (dd, J=8.3, 2.0 Hz, 1H), 6.27 (d, J=1.5 Hz, 1H), 4.90 (s, 2H), 3.88-4.08 (m, 2H), 3.79 (d, J=8.2 Hz, 2H), 3.48-3.75 (m, 8H), 3.27-3.44 (m, 2H), 2.97 (s, 2H), 2.71-2.84 (m, 4H), 2.48-2.72 (m, 2H), 1.15 (d, J=6.2 Hz, 3H).

Example 16

5-[(2S,6R)-2-[[6-[(3R,4R)-3-amino-4-methoxy-pyrrolidin-1-yl]spiro[1H-isobenzofuran-3,3'-azetidine]-1'-yl]methyl]-6-methyl-morpholin-4-yl]-2-deuterio-quinoline-8-carbonitrile

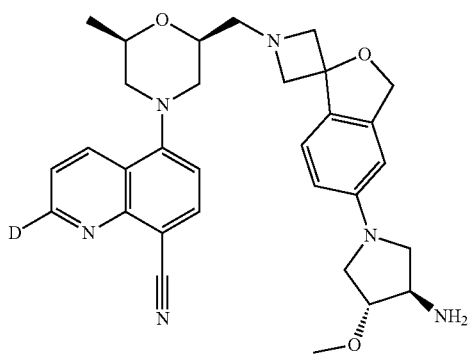 [SMILES: [2H]c1ccc2c(N3C[C@H](CN4CC5(C4)OCc4cc(N6C[C@@H](N)[C@H](OC)C6)ccc45)O[C@H](C)C3)ccc(C#N)c2n1]

The title compound was prepared in analogy to the preparation of Example 1 by using tert-butyl N-[(3R,4R)-4-methoxypyrrolidin-3-yl]carbamate (PharmaBlock, PBZ4728, CAS: 1932066-52-8) and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 16 (9 mg) was obtained as a yellow solid. MS: calc'd 542 (MH+), measured 542 (MH+). $^1$H NMR (400 MHz, METHANOL-d4) δ 8.55 (d, J=8.6 Hz, 1H), 8.05 (d, J=8.1 Hz, 1H), 7.53 (d, J=8.6 Hz, 1H), 7.35 (d, J=8.3 Hz, 1H), 7.15 (d, J=8.1 Hz, 1H), 6.51 (dd, J=8.4, 2.0 Hz, 1H), 6.34 (d, J=1.6 Hz, 1H), 4.90 (s, 2H), 3.88-4.02 (m, 2H), 3.70-3.80 (m, 1H), 3.58-3.68 (m, 5H), 3.37-3.52 (m, 2H), 3.24-3.35 (m, 4H), 3.02-3.20 (m, 2H), 2.49-2.82 (m, 4H), 1.15 ppm (d, J=6.4 Hz, 3H).

Example 17

5-[(2S,6R)-2-[[6-[(4aR,7aR)-3,4,4a,5,7,7a-hexahydro-2H-pyrrolo[3,4-b][1,4]oxazin-6-yl]spiro[1H-isobenzofuran-3,3'-azetidine]-1'-yl]methyl]-6-methyl-morpholin-4-yl]-2-deuterio-quinoline-8-carbonitrile

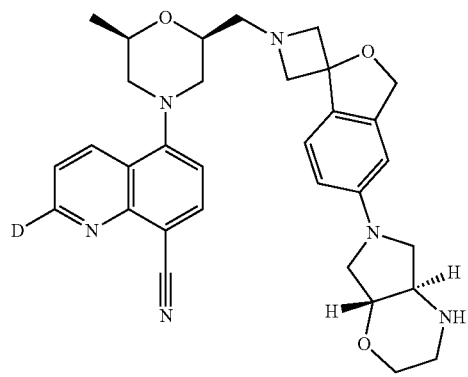 [SMILES: [2H]c1ccc2c(N3C[C@H](CN4CC5(C4)OCc4cc(N6C[C@H]7NCCO[C@@H]7C6)ccc45)O[C@H](C)C3)ccc(C#N)c2n1]

The title compound was prepared in analogy to the preparation of Example 1 by using tert-butyl (4aR,7aR)-3,4a,5,6,7,7a-hexahydro-2H-pyrrolo[3,4-b][1,4]oxazine-4-carboxylate (PharmaBlock, PBXA8123, CAS: 1932337-68-2) and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 17 (9 mg) was obtained as a yellow solid. MS: calc'd 554 (MH+), measured 554 (MH+). $^1$H NMR (400 MHz, METHANOL-d4) δ 8.55 (d, J=8.6 Hz, 1H), 8.05 (d, J=8.1 Hz, 1H), 7.53 (d, J=8.6 Hz, 1H), 7.34 (d, J=8.4 Hz, 1H), 7.16 (d, J=8.1 Hz, 1H), 6.46 (dd, J=8.5, 1.9 Hz, 1H), 6.29 (d, J=1.5 Hz, 1H), 4.91 (s, 2H), 3.82-4.07 (m, 3H), 3.62-3.80 (m, 5H), 3.26-3.59 (m, 6H), 2.82-3.12 (m, 6H), 2.50-2.76 (m, 2H), 1.15 (d, J=6.2 Hz, 3H).

Example 18

2-deuterio-5-[(2R,6S)-2-methyl-6-[(6-piperazin-1-ylspiro[1H-isobenzofuran-3,3'-azetidine]-1'-yl)methyl]morpholin-4-yl]quinoline-8-carbonitrile

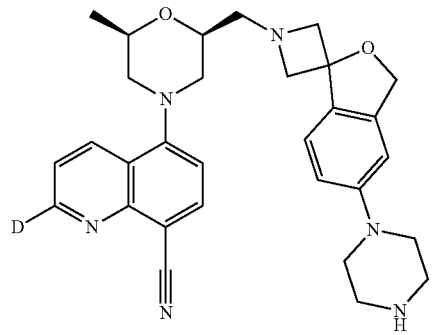 [SMILES: [2H]c1ccc2c(N3C[C@H](CN4CC5(C4)OCc4cc(N6CCNCC6)ccc45)O[C@H](C)C3)ccc(C#N)c2n1]

The title compound was prepared in analogy to the preparation of Example 1 by using tert-butyl piperazine-1-carboxylate and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 18 (2 mg) was obtained as a yellow solid. MS: calc'd 512 (MH$^+$), measured 512 (MH$^+$). $^1$H NMR (400 MHz, METHANOL-d4) δ 8.55 (d, J=8.6 Hz, 1H), 8.06 (d, J=7.9 Hz, 1H), 7.53 (d, J=8.6 Hz, 1H), 7.45 (d, J=8.4 Hz, 1H), 7.16 (d, J=8.1 Hz, 1H), 6.93 (dd, J=8.3, 2.2 Hz, 1H), 6.79 (d, J=1.3 Hz, 1H), 4.92 (s, 2H), 3.86-4.12 (m, 2H), 3.72 (m, 4H), 3.28-3.44 (m, 6H), 3.08-3.17 (m, 4H), 2.51-2.80 (m, 4H), 1.14 (d, J=6.2 Hz, 3H).

Example 19

4-[(2S,6R)-2-[[6-(3-aminoazetidin-1-yl)spiro[1H-isobenzofuran-3,3'-azetidine]-1'-yl]methyl]-6-methyl-morpholin-4-yl]pyrazolo[1,5-a]pyridine-7-carbonitrile

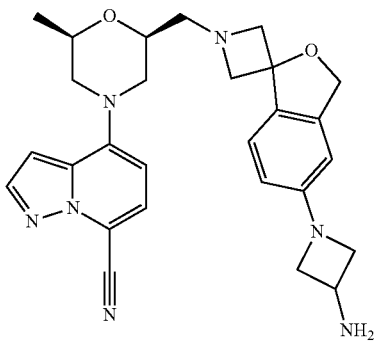 [SMILES: C[C@@H]1CN(c2ccc(C#N)n3nccc23)C[C@H](CN2CC3(C2)OCc2cc(N4CC(N)C4)ccc23)O1]

The title compound was prepared in analogy to the preparation of Example 1 by using [(2R,6R)-4-(7-cyanopyrazolo[1,5-a]pyridin-4-yl)-6-methyl-morpholin-2-yl]methyl trifluoromethanesulfonate (Intermediate F) and tert-Butyl azetidin-3-ylcarbamate (CAS: 91188-13-5, vendor: BePharm) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl (3-methylazetidin-3-yl)carbamate (compound 1d). Example 19 (12 mg) was obtained as a light yellow solid. MS: calc'd 486 (MH$^+$), measured 486 (MH$^+$). $^1$H NMR (METHANOL-d$_4$, 400 MHz) δ 8.02 (d, J=2.3 Hz, 1H), 7.46 (dd, J=6.0, 8.1 Hz, 2H), 6.87 (d, J=2.3 Hz, 1H), 6.59 (d, J=7.9 Hz, 1H), 6.49 (dd, J=1.7, 8.3 Hz, 1H), 6.34 (s, 1H), 4.97 (s, 2H), 4.58 (br s, 3H), 4.12 (t, J=7.3 Hz, 2H), 3.9-3.9 (m, 3H), 3.73 (br d, J=12.0 Hz, 1H), 3.6-3.7 (m, 3H), 3.5-3.5 (m, 3H), 2.7-2.8 (m, 2H), 2.6-2.7 (m, 1H), 1.24 (d, J=6.2 Hz, 3H).

Example 20

5-[(2S,6R)-2-[[3-(3-aminoazetidin-1-yl)spiro[5H-furo[3,4-b]pyridine-7,3'-azetidine]-1'-yl]methyl]-6-methyl-morpholin-4-yl]-2-deuterio-quinoline-8-carbonitrile

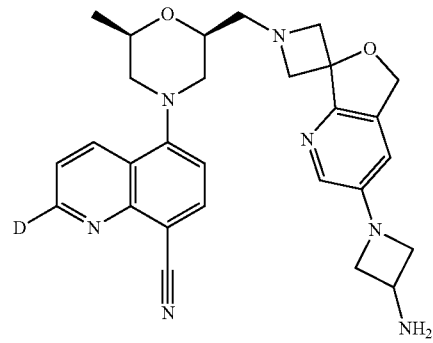

The title compound was prepared in analogy to the preparation of Example 1 by using tert-butyl N-(azetidin-3-yl)carbamate and tert-butyl 3-bromospiro[5H-furo[3,4-b]pyridine-7,3'-azetidine]-1'-carboxylate (CAS: 1575836-59-7, Cat. #: PBU1967, Vendor: Pharmablock) and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and tert-butyl 6-bromospiro[1H-isobenzofuran-3,3'-azetidine]-1'-carboxylate (compound 1a) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 20 (3 mg) was obtained as a yellow solid. MS: calc'd 499 (MH$^+$), measured 499 (MH$^+$). $^1$H NMR (400 MHz, METHANOL-d$_4$) δ 8.66 (d, J=8.6 Hz, 1H), 8.16 (d, J=7.9 Hz, 1H), 7.75 (d, J=2.6 Hz, 1H), 7.65 (d, J=8.7 Hz, 1H), 7.27 (d, J=8.1 Hz, 1H), 6.81 (d, J=2.4 Hz, 1H), 5.04 (s, 2H), 4.22 (t, J=7.4 Hz, 2H), 3.91-4.12 (m, 3H), 3.67-3.82 (m, 4H), 3.60 (dd, J=7.7, 5.6 Hz, 2H), 3.35-3.50 (m, 5H), 2.55-2.92 (m, 4H).

Example 21

5-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]-2-deuterio-quinoline-8-carbonitrile

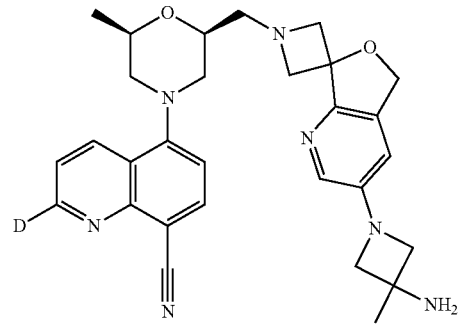 [SMILES: [2H]c1ccc2c(N3C[C@H](CN4CC5(C4)OCc4cc(N6CC(C)(N)C6)cnc45)O[C@H](C)C3)ccc(C#N)c2n1]

The title compound was prepared in analogy to the preparation of Example 1 by using tert-butyl 3-bromospiro[5H-furo[3,4-b]pyridine-7,3'-azetidine]-1'-carboxylate and [(2R,6R)-4-(8-cyano-2-deuterio-5-quinolyl)-6-methyl-morpholin-2-yl]methyl trifluoromethanesulfonate (Intermediate L) instead of tert-butyl 6-bromospiro[1H-isobenzofuran-3,3'-azetidine]-1'-carboxylate (compound 1a) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 21 (10 mg) was obtained as a yellow solid. MS: calc'd 513 (MH$^+$), measured 513 (MH$^+$). $^1$H NMR (400 MHz, METHANOL-d$_4$) δ 8.66 (d, J=8.6 Hz, 1H), 8.16 (d, J=8.1 Hz, 1H), 7.75 (d, J=2.4 Hz, 1H), 7.65 (d, J=8.7 Hz, 1H), 7.27 (d, J=8.1 Hz, 1H), 6.82 (d, J=2.4 Hz, 1H), 5.04 (s, 2H), 3.95-4.18 (m, 2H), 3.83-3.90 (m, 2H), 3.61-3.80 (m, 6H), 3.36-3.52 (m, 2H), 2.56-2.93 (m, 4H), 1.54 (s, 3H), 1.24 (d, J=6.2 Hz, 3H).

Example 22

3-fluoro-4-[(2R,6S)-2-methyl-6-[[3-(6-methyl-2,6-diazaspiro[3.3]heptan-2-yl)spiro[5H-furo[3,4-b]pyridine-7,3'-azetidine]-1'-yl]methyl]morpholin-4-yl]pyrazolo[1,5-a]pyridine-7-carbonitrile

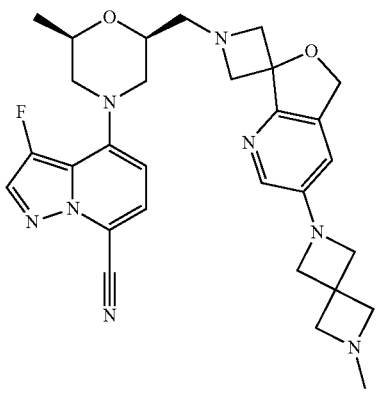 [SMILES: C[C@@H]1CN(c2ccc(C#N)n3ncc(F)c23)C[C@H](CN2CC3(C2)OCc2cc(N4CC5(CN(C)C5)C4)cnc23)O1]

The title compound was prepared in analogy to the preparation of Example 1 by using 2-methyl-2,6-diazaspiro[3.3]heptane and tert-butyl 3-bromospiro[5H-furo[3,4-b]pyridine-7,3'-azetidine]-1'-carboxylate instead of tert-butyl (3-methylazetidin-3-yl)carbamate (compound 1d) and tert-butyl 6-bromospiro[1H-isobenzofuran-3,3'-azetidine]-1'-carboxylate (compound 1a). Example 22 (15 mg) was obtained as a yellow solid. MS: calc'd 545 (MH$^+$), measured 545 (MH$^+$). $^1$H NMR (400 MHz, METHANOL-d$_4$) δ 7.91 (d, J=3.7 Hz, 1H), 7.76 (s, 1H), 7.35 (d, J=7.9 Hz, 1H), 6.75 (d, J=2.4 Hz, 1H), 6.46 (d, J=7.9 Hz, 1H), 5.02 (s, 2H), 4.31-4.61 (m, 6H), 4.00-4.23 (m, 7H), 3.79-3.94 (m, 1H), 3.41-3.67 (m, 4H), 2.85 (s, 3H), 2.48-2.74 (m, 2H), 1.18 (d, J=6.2 Hz, 3H).

Example 23

5-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-2-deuterio-quinoline-8-carbonitrile

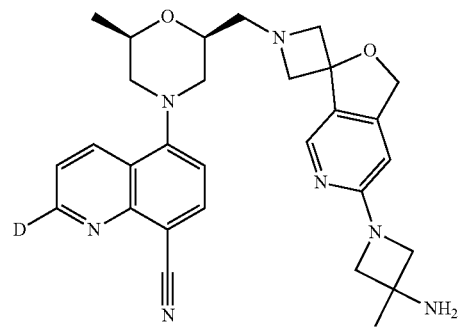

The title compound was prepared in analogy to the preparation of Example 1 by using [(2R,6R)-4-(8-cyano-2-deuterio-5-quinolyl)-6-methyl-morpholin-2-yl]methyl trifluoromethanesulfonate (Intermediate L) and tert-Spiro[azetidine-3,3'(1'H)-furo[3,4-c]pyridine]-1-carboxylic acid, 6'-chloro-, 1,1-dimethylethyl ester (CAS: 1575836-95-1, vendor: PharmaBlock) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl 6-bromospiro[1H-isobenzofuran-3,3'-azetidine]-1'-carboxylate (compound 1a). Example 23 (38 mg) was obtained as a light yellow solid. MS: calc'd 513 (MH$^+$), measured 513 (MH$^+$). $^1$H NMR (METHANOL-d$_4$, 400 MHz) δ 8.63 (d, J=8.7 Hz, 1H), 8.54 (s, 1H), 8.13 (d, J=7.9 Hz, 1H), 7.63 (d, J=8.6 Hz, 1H), 7.25 (d, J=8.1 Hz, 1H), 6.7-6.8 (m, 1H), 5.17 (s, 2H), 4.81 (br d, J=8.4 Hz, 2H), 4.63 (br dd, J=12.0, 17.2 Hz, 2H), 4.4-4.4 (m, 2H), 4.3-4.4 (m, 3H), 4.1-4.2 (m, 1H), 3.6-3.7 (m, 1H), 3.5-3.6 (m, 1H), 3.41 (br t, J=11.5 Hz, 2H), 2.79 (t, J=11.1 Hz, 1H), 2.70 (dd, J=10.4, 12.1 Hz, 1H), 1.73 (s, 3H), 1.28 (d, J=6.2 Hz, 3H).

Example 24

4-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-3-fluoro-pyrazolo[1,5-a]pyridine-7-carbonitrile

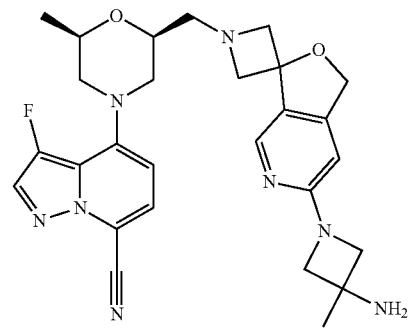 [SMILES: C[C@@H]1CN(c2ccc(C#N)n3ncc(F)c23)C[C@H](CN2CC3(C2)OCc2cc(N4CC(C)(N)C4)ncc23)O1]

The title compound was prepared in analogy to the preparation of Example 1 by using tert-Spiro[azetidine-3,3' (1'H)-furo[3,4-c]pyridine]-1-carboxylic acid, 6'-chloro-, 1,1-dimethylethyl ester (CAS: 1575836-95-1, vendor: PharmaBlock) instead of tert-butyl 6-bromospiro[1H-isobenzofuran-3,3'-azetidine]-1'-carboxylate (compound 1a). Example 24 (3 mg) was obtained as a light yellow solid. MS: calc'd 519 (MH+), measured 519 (MH+). $^1$H NMR (METHANOL-d$_4$, 400 MHz) δ 8.47 (s, 1H), 8.01 (d, J=3.5 Hz, 1H), 7.44 (d, J=7.8 Hz, 1H), 6.55 (d, J=7.9 Hz, 1H), 6.51 (d, J=0.7 Hz, 1H), 5.11 (s, 2H), 4.6-4.7 (m, 2H), 4.5-4.6 (m, 2H), 4.2-4.2 (m, 2H), 4.1-4.2 (m, 3H), 3.9-4.0 (m, 1H), 3.5-3.7 (m, 4H), 2.6-2.8 (m, 2H), 1.69 (s, 3H), 1.3-1.3 (m, 3H).

Example 25

4-[(2S,6R)-2-[[6-(3-amino-3-methyl-azetidin-1-yl) spiro[1H-furo[3,4-c]pyridine-3,3'-azetidine]-1'-yl] methyl]-6-methyl-morpholin-4-yl]pyrazolo[1,5-a] pyridine-7-carbonitrile

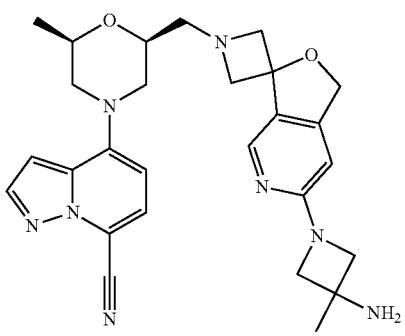 [SMILES: C[C@@H]1CN(c2ccc(C#N)n3nccc23)C[C@H](CN2CC3(C2)OCc2cc(N4CC(C)(N)C4)ncc23)O1]

The title compound was prepared in analogy to the preparation of Example 1 by using [(2R,6R)-4-(7-cyanopyrazolo[1,5-a]pyridin-4-yl)-6-methyl-morpholin-2-yl]methyl trifluoromethanesulfonate (Intermediate F) and tert-Spiro[azetidine-3,3'(1'H)-furo[3,4-c]pyridine]-1-carboxylic acid, 6'-chloro-, 1,1-dimethylethyl ester (CAS: 1575836-95-1, vendor: PharmaBlock) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl 6-bromospiro[1H-isobenzofuran-3,3'-azetidine]-1'-carboxylate (compound 1a). Example 25 (22 mg) was obtained as a light yellow solid. MS: calc'd 501 (MH+), measured 501 (MH+). $^1$H NMR (METHANOL-d$_4$, 400 MHz) δ 8.52 (s, 1H), 8.03 (d, J=2.3 Hz, 1H), 7.46 (d, J=7.9 Hz, 1H), 6.89 (d, J=2.4 Hz, 1H), 6.71 (s, 1H), 6.62 (d, J=7.9 Hz, 1H), 5.16 (s, 2H), 4.7-4.8 (m, 2H), 4.62 (br dd, J=12.0, 17.4 Hz, 2H), 4.38 (d, J=9.9 Hz, 2H), 4.2-4.3 (m, 2H), 4.2-4.2 (m, 2H), 3.9-4.0 (m, 1H), 3.7-3.8 (m, 2H), 3.7-3.7 (m, 1H), 3.5-3.6 (m, 1H), 2.77 (dd, J=10.8, 11.9 Hz, 1H), 2.70 (dd, J=10.6, 12.3 Hz, 1H), 1.73 (s, 3H), 1.29 (d, J=6.2 Hz, 3H).

Example 26

4-[(2S,6R)-2-[[3-(3-amino-3-methyl-azetidin-1-yl) spiro[5H-furo[3,4-b]pyridine-7,3'-azetidine]-1'-yl] methyl]-6-methyl-morpholin-4-yl]pyrazolo[1,5-a] pyridine-7-carbonitrile

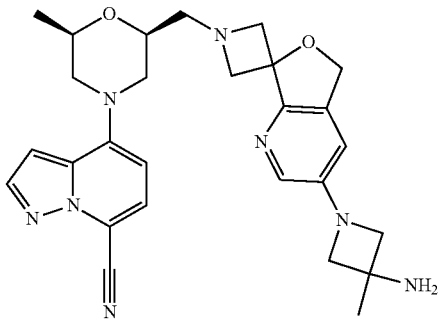 [SMILES: C[C@@H]1CN(c2ccc(C#N)n3nccc23)C[C@H](CN2CC3(C2)OCc2cc(N4CC(C)(N)C4)cnc23)O1]

The title compound was prepared in analogy to the preparation of Example 1 by using [(2R,6R)-4-(7-cyanopyrazolo[1,5-a]pyridin-4-yl)-6-methyl-morpholin-2-yl]methyl trifluoromethanesulfonate (Intermediate F) and tert-butyl 3-bromospiro[5H-furo[3,4-b]pyridine-7,3'-azetidine]-1-carboxylate (CAS: 1575836-59-7, vendor: PharmaBlock) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl 6-bromospiro[1H-isobenzofuran-3,3'-azetidine]-1'-carboxylate (compound 1a). Example 26 (7 mg) was obtained as a light yellow solid. MS: calc'd 501 (MH+), measured 501 (MH+). $^1$H NMR (METHANOL-d$_4$, 400 MHz) δ 8.04 (d, J=2.3 Hz, 1H), 7.92 (d, J=1.5 Hz, 1H), 7.49 (d, J=8.1 Hz, 1H), 6.9-6.9 (m, 2H), 6.64 (d, J=8.1 Hz, 1H), 5.13 (s, 2H), 4.6-4.7 (m, 1H), 4.5-4.6 (m, 2H), 4.1-4.2 (m, 1H), 4.10 (d, J=8.6 Hz, 2H), 4.0-4.0 (m, 3H), 3.7-3.9 (m, 3H), 3.5-3.6 (m, 2H), 2.7-2.8 (m, 2H), 1.69 (s, 3H), 1.30 (d, J=6.1 Hz, 3H).

Example 28

5-[(2S,6R)-2-[[6-[(4aR,7aR)-3,4,4a,5,7,7a-hexahydro-2H-pyrrolo[3,4-b][1,4]oxazin-6-yl]spiro[1H-furo[3,4-c]pyridine-3,3'-azetidine]-1'-yl]methyl]-6-methyl-morpholin-4-yl]-2-deuterio-quinoline-8-carbonitrile

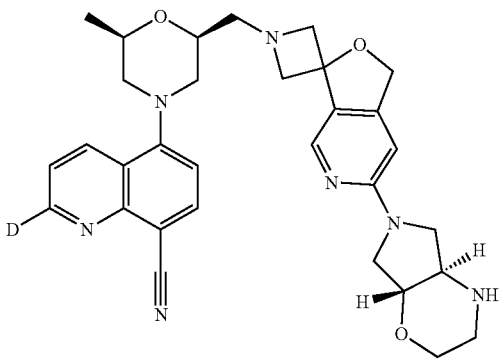 [SMILES: [2H]c1ccc2c(N3C[C@H](CN4CC5(C4)OCc4cc(N6C[C@H]7NCCO[C@@H]7C6)ncc45)O[C@H](C)C3)ccc(C#N)c2n1]

The title compound was prepared in analogy to the preparation of Example 1 by using tert-butyl (4aR,7aR)-3,4a,5,6,7,7a-hexahydro-2H-pyrrolo[3,4-b][1,4]oxazine-4-carboxylate (PharmaBlock, PBXA8123, CAS: 1932337-68-2), [(2R,6R)-4-(8-cyano-2-deuterio-5-quinolyl)-6-methyl-morpholin-2-yl]methyl trifluoromethanesulfonate (Intermediate L) and tert-Spiro[azetidine-3,3'(1'H)-furo[3,4-c]pyridine]-1-carboxylic acid, 6'-chloro-, 1,1-dimethylethyl ester (CAS: 1575836-95-1, vendor: PharmaBlock) instead of tert-butyl (3-methylazetidin-3-yl)carbamate (compound 1d), [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl 6-bromospiro[1H-isobenzofuran-3,3'-azetidine]-1'-carboxylate (compound 1a). Example 28 (2 mg) was obtained as a light yellow solid. MS: calc'd 555 (MH⁺), measured 555 (MH⁺). $^1$H NMR (400 MHz, METHANOL-$d_4$) δ 8.67 (d, J=8.7 Hz, 1H), 8.34 (s, 1H), 8.18 (d, J=8.1 Hz, 1H), 7.66 (d, J=8.6 Hz, 1H), 7.28 (d, J=8.1 Hz, 1H), 6.39 (s, 1H), 4.99 (s, 2H), 4.11-3.96 (m, 3H), 3.83-3.72 (m, 3H), 3.71-3.62 (m, 5H), 3.52-3.44 (m, 1H), 3.43-3.37 (m, 1H), 3.17-3.12 (m, 1H), 3.06-2.92 (m, 3H), 2.80-2.77 (m, 2H), 2.71-2.64 (m, 1H), 2.24-2.18 (m, 1H), 2.07-2.03 (m, 1H), 1.26 (d, J=6.4 Hz, 3H).

Example 29

5-[(2S,6R)-2-[[3-[(4aR,7aR)-3,4,4a,5,7,7a-hexahydro-2H-pyrrolo[3,4-b][1,4]oxazin-6-yl]spiro[5H-furo[3,4-b]pyridine-7,3'-azetidine]-1'-yl]methyl]-6-methyl-morpholin-4-yl]-2-deuterio-quinoline-8-carbonitrile

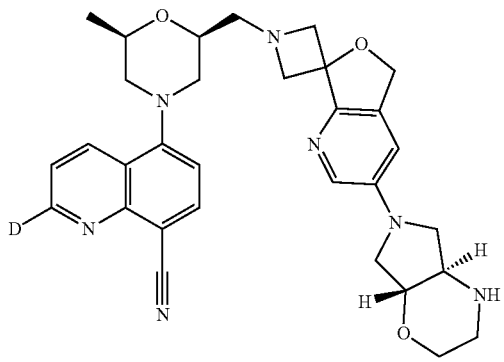 [SMILES: [2H]c1ccc2c(N3C[C@H](CN4CC5(C4)OCc4cc(N6C[C@H]7NCCO[C@@H]7C6)cnc45)O[C@H](C)C3)ccc(C#N)c2n1]

The title compound was prepared in analogy to the preparation of Example 1 by using tert-butyl (4aR,7aR)-3,4a,5,6,7,7a-hexahydro-2H-pyrrolo[3,4-b][1,4]oxazine-4-carboxylate (PharmaBlock, PBXA8123, CAS: 1932337-68-2) and tert-butyl 3-bromospiro[5H-furo[3,4-b]pyridine-7,3'-azetidine]-1'-carboxylate (CAS: 1575836-59-7, PBU1967, Vendor: Pharmablock) and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and tert-butyl 6-bromospiro[1H-isobenzofuran-3,3'-azetidine]-1'-carboxylate (compound 1a) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 29 (13 mg) was obtained as a yellow solid. MS: calc'd 555 (MH⁺), measured 555 (MH⁺). $^1$H NMR (400 MHz, METHANOL-$d_4$) δ 8.54 (d, J=8.6 Hz, 1H), 8.04 (d, J=8.1 Hz, 1H), 7.73 (d, J=2.4 Hz, 1H), 7.53 (d, J=8.6 Hz, 1H), 7.15 (d, J=8.1 Hz, 1H), 6.76 (d, J=2.4 Hz, 1H), 4.94 (s, 2H), 3.84-4.05 (m, 3H), 3.43-3.78 (m, 8H), 3.25-3.40 (m, 2H), 2.48-3.15 (m, 9H), 1.13 ppm (d, J=6.2 Hz, 3H).

Example 31

5-[(2S,6R)-2-[[3-[(3R,4R)-3-amino-4-methoxy-pyrrolidin-1-yl]spiro[5H-furo[3,4-b]pyridine-7,3'-azetidine]-1'-yl]methyl]-6-methyl-morpholin-4-yl]-2-deuterio-quinoline-8-carbonitrile

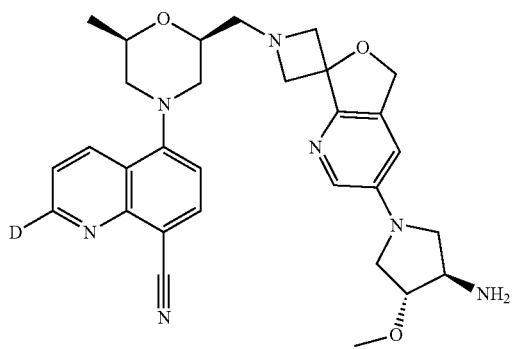 [SMILES: [2H]c1ccc2c(N3C[C@H](CN4CC5(C4)OCc4cc(N6C[C@@H](N)[C@H](OC)C6)cnc45)O[C@H](C)C3)ccc(C#N)c2n1]

The title compound was prepared in analogy to the preparation of Example 1 by using tert-butyl N-[(3R,4R)-4-methoxypyrrolidin-3-yl]carbamate (PharmaBlock, PBZ4728, CAS: 1932066-52-8) and tert-butyl 3-bromospiro[5H-furo[3,4-b]pyridine-7,3'-azetidine]-1'-carboxylate (CAS: 1575836-59-7, PBU1967, Vendor: Pharmablock) and [(2R,6R)-4-(8-cyano-2-deuterio-5-quinolyl)-6-methyl-morpholin-2-yl]methyl trifluoromethanesulfonate (Intermediate L) instead of tert-butyl (3-methylazetidin-3-yl)carbamate (compound 1d) and tert-butyl 6-bromospiro[1H-isobenzofuran-3,3'-azetidine]-1'-carboxylate (compound 1a) and [(2R,6R)-4-(7-cyano-3-fluoro-pyrazolo[1,5-a]pyridin-4-yl)-6-methyl-morpholin-2-yl]methyl trifluoromethanesulfonate (Intermediate E). Example 31 (13 mg) was obtained as a yellow solid. MS: calc'd 543 (MH⁺), measured 543 (MH⁺). $^1$H NMR (400 MHz, METHANOL-d4) δ 8.54 (d, J=8.7 Hz, 1H), 8.05 (d, J=7.9 Hz, 1H), 7.75 (d, J=2.4 Hz, 1H), 7.53 (d, J=8.7 Hz, 1H), 7.15 (d, J=8.1 Hz, 1H), 6.79 (d, J=2.4 Hz, 1H), 4.94 (s, 2H), 3.87-4.00 (m, 2H), 3.57-3.78 (m, 6H), 3.39-3.55 (m, 2H), 3.23-3.38 (m, 6H), 2.97-3.09 (m, 1H), 2.44-2.81 (m, 4H), 1.13 ppm (d, J=6.2 Hz, 3H).

Example 32

5-[(2S,6R)-2-[[6-(3-aminoazetidin-1-yl)spiro[1H-furo[3,4-c]pyridine-3,3'-azetidine]-1'-yl]methyl]-6-methyl-morpholin-4-yl]-2-deuterio-quinoline-8-carbonitrile

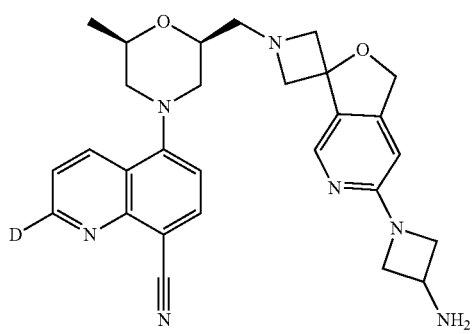 [SMILES: [2H]c1ccc2c(N3C[C@H](CN4CC5(C4)OCc4cc(N6CC(N)C6)ncc45)O[C@H](C)C3)ccc(C#N)c2n1]

The title compound was prepared in analogy to the preparation of Example 1 by using [(2R,6R)-4-(8-cyano-2-deuterio-5-quinolyl)-6-methyl-morpholin-2-yl]methyl trifluoromethanesulfonate (Intermediate L) and tert-Spiro[azetidine-3,3'(1'H)-furo[3,4-c]pyridine]-1-carboxylic acid, 6'-chloro-, 1,1-dimethylethyl ester (CAS: 1575836-95-1, vendor: PharmaBlock) instead of [(2R,6R)-4-(7-cyano-3-fluoro-pyrazolo[1,5-a]pyridin-4-yl)-6-methyl-morpholin-2-yl]methyl trifluoromethanesulfonate (Intermediate E) and tert-butyl 6-bromospiro[1H-isobenzofuran-3,3'-azetidine]-1'-carboxylate (compound 1a). Example 32 (2 mg) was obtained as a light yellow solid. MS: calc'd 499 (MH$^+$), measured 499 (MH$^+$). $^1$H NMR (400 MHz, METHANOL-d$_4$) δ 8.65 (d, J=8.6 Hz, 1H), 8.32 (s, 1H), 8.15 (d, J=7.9 Hz, 1H), 7.63 (d, J=8.7 Hz, 1H), 7.25 (d, J=8.1 Hz, 1H), 6.32 (s, 1H), 4.96 (s, 2H), 4.26 (d, J=7.6 Hz, 1H), 4.09-4.02 (m, 2H), 3.78 (dd, J=8.1, 4.8 Hz, 2H), 3.72-3.62 (m, 4H), 3.49-3.41 (m, 2H), 3.40-3.35 (m, 2H), 2.81-2.71 (m, 3H), 2.69-2.62 (m, 1H), 1.24 (d, J=6.2 Hz, 3H).

Example 33

4-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]-3-fluoro-pyrazolo[1,5-a]pyridine-7-carbonitrile

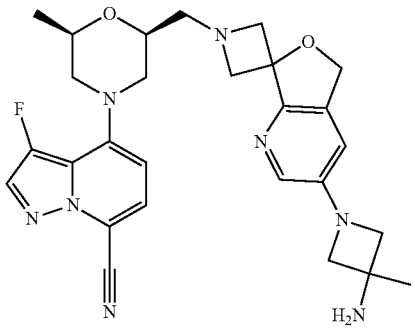 [SMILES: C[C@@H]1CN(c2ccc(C#N)n3ncc(F)c23)C[C@H](CN2CC3(C2)OCc2cc(N4CC(C)(N)C4)cnc23)O1]

The title compound was prepared in analogy to the preparation of Example 1 by using tert-butyl 3-bromospiro[5H-furo[3,4-b]pyridine-7,3-azetidine]-1-carboxylate (CAS: 1575836-59-7, vendor: PharmaBlock) instead of tert-butyl 6-bromospiro[1H-isobenzofuran-3,3'-azetidine]-1'-carboxylate (compound 1a). Example 33 (3 mg) was obtained as a light yellow solid. MS: calc'd 519 (MH$^+$), measured 519 (MH$^+$). $^1$H NMR (400 MHz, METHANOL-d$_4$) δ 7.9-8.0 (m, 1H), 7.8-7.9 (m, 1H), 7.35 (d, 1H, J=7.9 Hz), 6.82 (d, 1H, J=2.6 Hz), 6.3-6.5 (m, 1H), 5.04 (s, 2H), 3.9-4.1 (m, 5H), 3.3-3.6 (m, 6H), 2.5-2.8 (m, 2H), 2.96-3.10 (m, 3H), 1.59 (s, 3H), 1.1-1.3 (m, 3H).

Example 34

The following tests were carried out in order to determine the activity of the compounds of formula (I) and (Ia) in HEK293-Blue-hTLR-7/8/9 cells assay.

HEK293-Blue-hTLR-7 cells assay:

A stable HEK293-Blue-hTLR-7 cell line was purchased from InvivoGen (Cat. #: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signaling pathway that TLR7 activation leads to downstream NF-κB activation has been widely accepted, and therefore similar reporter assay was modified for evaluating TLR7 antagonist.

HEK293-Blue-hTLR-8 cells assay:

A stable HEK293-Blue-hTLR-8 cell line was purchased from InvivoGen (Cat. #: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR8 activation leads to downstream NF-κB activation has been widely accepted, and therefore similar reporter assay was modified for evaluating TLR8 antagonist.

HEK293-Blue-hTLR-9 cells assay: A stable HEK293-Blue-hTLR-9 cell line was purchased from InvivoGen (Cat. #: hkb-htlr9, San Diego, California, USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, California, USA), for incubation of 20 hrs. The cell culture supernatant SEAP reporter activity was determined using QUANTI-Blue™ kit (Cat. #: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a $CO_2$ incubator for 20 hrs. Then 20 μL of the supernatant from each well was incubated with 180 μL Quanti-blue substrate solution at 37° C. for 2 h and the absorbance was read at 620-655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) or (a) have human TLR7 and/or TLR8 inhibitory activities ($IC_{50}$ value)<0.5 μM. Moreover, some compounds also have human TLR9 inhibitory activity<0.5 μM. Activity data of the compounds of the present invention were shown in Table 2.

TABLE 2

The activity of the compounds of present invention in HEK293-Blue-hTLR-7/8/9 cells assays

| Example No | HEK/hTLR7 $IC_{50}$ (μM) | HEK/hTLR8 $IC_{50}$ (μM) | HEK/hTLR9 $IC_{50}$ (μM) |
|---|---|---|---|
| 1 | 0.012 | 0.082 | 0.131 |
| 2 | 0.010 | 0.025 | 0.045 |
| 3 | 0.020 | 0.051 | 0.047 |
| 4 | 0.016 | 0.035 | 0.096 |
| 5 | 0.019 | 0.022 | 0.094 |
| 6 | 0.008 | 0.024 | 0.090 |
| 7 | 0.015 | 0.058 | 0.068 |
| 8 | 0.005 | 0.040 | 0.032 |
| 9 | 0.005 | 0.045 | 0.084 |
| 10 | 0.008 | 0.142 | 0.061 |
| 11 | 0.003 | 0.019 | 0.051 |
| 12 | 0.010 | 0.037 | 0.103 |
| 13 | 0.010 | 0.409 | 0.068 |
| 14 | 0.003 | 0.017 | 0.057 |
| 15 | 0.008 | 0.009 | 0.032 |
| 16 | 0.019 | 0.013 | 0.032 |
| 17 | 0.015 | 0.009 | 0.032 |
| 18 | 0.007 | 0.010 | 0.032 |
| 19 | 0.019 | 0.099 | 0.036 |
| 20 | 0.009 | 0.030 | 0.032 |
| 21 | 0.007 | 0.017 | 0.055 |
| 22 | 0.009 | 0.064 | 0.057 |
| 23 | 0.005 | 0.016 | 0.040 |
| 24 | 0.016 | 0.059 | 0.086 |
| 25 | 0.023 | 0.120 | 0.070 |
| 26 | 0.024 | 0.234 | 0.080 |
| 28 | 0.007 | 0.025 | 0.160 |
| 29 | 0.004 | 0.010 | 0.039 |
| 31 | 0.007 | 0.030 | 0.079 |
| 32 | 0.004 | 0.022 | 0.244 |
| 33 | 0.013 | 0.024 | 0.227 |

Example 35 hERG Channel Inhibition Assay:

The hERG channel inhibition assay is a highly sensitive measurement that identifies compounds exhibiting hERG inhibition related to cardiotoxicity in vivo. The hERG K+ channels were cloned in humans and stably expressed in a CHO (Chinese hamster ovary) cell line. $CHO_{hERG}$ cells were used for patch-clamp (voltage-clamp, whole-cell) experiments. Cells were stimulated by a voltage pattern to activate hERG channels and conduct $I_{KhERG}$ Currents (rapid delayed outward rectifier potassium current of the hERG channel). After the cells were stabilized for a few minutes, the amplitude and kinetics of $I_{KhERG}$ were recorded at a stimulation frequency of 0.1 Hz, (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of $I_{KhERG}$ are recorded in each concentration of the drug which were compared to the control values (taken as 100%). (references: Redfern W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti M C, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26).

Results of hERG are given in Table 3. A safety ratio (hERG $IC_{20}/EC_{50}$)>30 suggests a sufficient window to differentiate the pharmacology by inhibiting TLR7/8/9 pathways from the potential hERG related cardiotoxicity. According to the calculation of hERG $IC_{20}$/TLR7/8/9 $IC_{50}$ below which serves as early selectivity index to assess hERG liability, obviously reference compounds ER-887258, ER-888285, ER-888286, R1 and R2 have much narrower safety window compared to the compounds of this invention.

TABLE 3 hERG and safety ratio results

| Example No | hERG $IC_{20}$ (μM) | hERG $IC_{50}$ (μM) | hERG $IC_{20}$/ TLR7 $IC_{50}$ | hERG $IC_{20}$/ TLR8 $IC_{50}$ | hERG $IC_{20}$/ TLR9 $IC_{50}$ |
|---|---|---|---|---|---|
| ER-887258 | 0.687 | 2.784 | 8.1 | N.A. | 0.3 |
| ER-888285 | 1.006 | 3.105 | 8.4 | N.A. | 0.5 |
| ER-888286 | 0.348 | 1.297 | 0.3 | N.A. | 0.2 |
| 2 | 9.9 | >20 | 990 | 396 | 220 |
| 11 | 6.2 | >20 | 2066 | 347 | 129 |
| 14 | >10 | >20 | >3333 | >588 | >175 |
| 21 | >10 | >20 | >1428 | >588 | >181 |

Example 36

The compounds would be desirable to have minimal DDI liabilities. Therefore, the effects of compounds of formula (I) of (Ia) on major CYP isoforms, e.g. CYP2C9, CYP2D6 and CYP3A4, are determined.

CYP Inhibition Assay

This is a high throughput screening assay used for assessment of reversible inhibition of CYP2C9, CYP2D6, and CYP3A4 activity of test compounds in human liver microsome (HLM) in early discovery stage.

TABLE 4

Chemicals and materials used in the CYP inhibition assay

| Substances | Description | Source | Cat. No. | Final Concentration in incubation |
|---|---|---|---|---|
| Human Liver Microsomes | | BD-Gentest | 452117 | 0.2 mg/mL |
| Diclofenac | CYP2C9 substrate | Sigma | D-6899 | 5 µM |
| 4'-Hydroxydiclofenac | CYP2C9 product | | | |
| 4'-OH-Diclofenac-13C6 | CYP2C9 internal standard | Becton Dickinson | 451006 | |
| Dextromethorphan | CYP2D6 substrate | Sigma | D-2531 | 5 µM |
| Dextrorphan | CYP2D6 product | | | |
| Dextrorphan-D3 | CYP2D6 internal standard | Promochem | CERD-041 | |
| Midazolam | CYP3A4 substrate | Roche | | 5 µM |
| 1'-Hydroxymidazolam | CYP3A4 product | | | |
| 1'-OH Midazolam-D4 | CYP3A4 internal standard | Roche | | |
| Sulfaphenazole | CYP2C9 inhibitor | | | 2 µM |
| Quinidine | CYP2D6 inhibitor | | | 0.5 µM |
| Ketoconazole | CYP3A4 inhibitor | | | 0.5 µM |

Procedure 10 mM DMSO stock solutions of test compounds were diluted in DMSO to generate 2 mM intermediate stock solution. 250 nL of intermediate stock solution were transferred in duplicate into 3 separate 384 well microtitre plates (assay-ready plates). A mixture of HLM and each substrate was made up. 45 µL of HLM substrate mix was then transferred to each well of an assay ready plate and mixed. The negative (solvent) and positive controls (standard inhibitor for each CYP) were included in each assay ready plate. The assay ready plate was warmed to 37° C. in an incubator over 10 minutes. 5 µL pre-warmed NADPH regenerating system was added to each incubation well to start the reaction. Final incubation volume was 50 µL. The assay plate then was placed back in the 37° C. incubator. After incubation (10 minutes for CYP2D6) for 5 minutes, incubates were quenched by addition of 50 µL 100% acetonitrile containing internal standards (400 ng/mL 13C6-4'-OH-Diclofenac, 20 ng/mL D3-Dextrorphan and 20 ng/mL D4-1'OH-Midazolam). The supernatants were collected for RapidFire/MS/MS analysis.

RapidFire online solid phase extraction/sample injection system (Agilent) coupled with API4000 triple quadrupole mass spectrometer (AB Sciex) were used for sample analysis. The mobile phase composed of acetonitrile and water supplemented with 0.1% formic acid. A C4 solid phase extraction cartridge is used for sample separation. MS detection is achieved in positive ion MRM mode.

Data analysis Peak areas for substrate, metabolite and internal standard are determined using the RapidFire integrator software (version 3.6.12009.12296). Peak area ratios (PAR) of metabolite and internal standard (stable-labelled metabolite) are then calculated. The measurement window for each experiment is then defined: PAR (0% activity) =average PAR for all incubations containing concentrated inhibitor; Par (100% activity)=average PAR for all incubations containing no inhibitor (DMSO controls); % Activity (test inhibitor)=[PAR (test inhibitor)-PAR (0% activity)]/[PAR (100% activity)-PAR (0% activity)]; % Inhibition (test inhibitor)=100-% Activity (test inhibitor).

The compounds of present invention were found to have low CYP inhibition for CYP2D6 determined in the assays described above.

TABLE 5

CYP inhibition of the compounds of this invention for CYP2D6

| Example No | CYP (%) 2C9/2D6/3A4 |
|---|---|
| ER-888286 | 29.5/52.5/5.5 |
| 7 | 0/-2/16.5 |
| 8 | -8.5/5/-8.5 |
| 11 | 4/5.5/12 |
| 17 | 3.5/18.5/14 |
| 20 | 13.5/13/40.5 |
| 21 | 4.5/5/12.5 |
| 24 | 21/3.5/-0.5 | percentage inhibition <0: not or weak inhibitor

The invention claimed is:

1. A compound of formula (I),

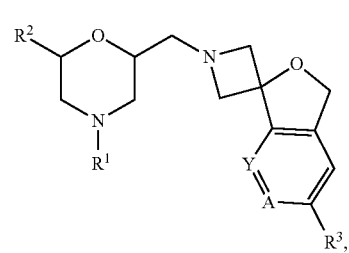

wherein:
R¹ is

[chemical structures]

wherein
- R⁴ is C₁₋₆alkyl, C₁₋₆alkoxy, haloC₁₋₆alkyl, halogen, nitro or cyano;
- R⁴ᵃ is C₁₋₆alkyl; or C₃₋₇cycloalkyl;
- R⁵, R⁵ᵃ and R⁵ᵇ are independently selected from H and deuterium; and
- R⁶ is H or halogen;
- R² is C₁₋₆alkyl;
- R³ is unsubstituted or substituted heterocyclyl; and
- Y and A are independently selected from CH and N;

or a pharmaceutically acceptable salt thereof.

2. A compound according to claim 1, wherein:
R¹ is

[chemical structures]

wherein
- R⁴ is cyano;
- R⁴ᵃ is C₁₋₆alkyl;
- R⁵ is H or deuterium; and
- R⁶ is H or halogen;
- R² is C₁₋₆alkyl;
- R³ is 2,6-diazaspiro[3.3]heptanyl; 3,4,4a,5,7,7a-hexahydro-2H-pyrrolo[3,4-b][1,4]oxazinyl; 5-oxa-2,8-diazaspiro[3.5]nonanyl; amino (C₁₋₆alkyl) azetidinyl; amino (C₁₋6alkyl) pyrrolidinyl; amino (C₁₋₆alkoxy) pyrrolidinyl; amino (hydroxy) pyrrolidinyl; aminoazetidinyl; C₁₋₆alkyl-2,6-diazaspiro[3.3]heptanyl; halopyrrolidinylamino or piperazinyl; and
- Y and A are independently selected from CH and N, provided that Y and A are not N simultaneously;

or a pharmaceutically acceptable salt thereof.

3. The compound of claim 1, wherein the compound of formula (I) is a compound of formula (Ia),

[chemical structure (Ia)]

wherein
R¹ is

[chemical structures]

wherein
- R⁴ is cyano;
- R⁴ᵃ is C₁₋₆alkyl;
- R⁵ is H or deuterium; and
- R⁶ is H or halogen;
- R² is C₁₋₆alkyl;

R³ is 2,6-diazaspiro[3.3]heptanyl; 3,4,4a,5,7,7a-hexahydro-2H-pyrrolo[3,4-b][1,4]oxazinyl; 5-oxa-2,8-diazaspiro[3.5]nonanyl; amino (C₁₋₆alkyl) azetidinyl; amino(C₁₋₆alkyl) pyrrolidinyl; amino(C₁₋₆alkoxy) pyrrolidinyl; amino (hydroxy) pyrrolidinyl; aminoazetidinyl; C₁₋₆alkyl-2,6-diazaspiro[3.3]heptanyl; halopyrrolidinylamino; or piperazinyl; and Y and A are independently selected from CH and N, provided that Y and A are not N simultaneously;

or a pharmaceutically acceptable salt thereof.

4. The compound of claim 2, or a pharmaceutically acceptable salt thereof, wherein R¹ is

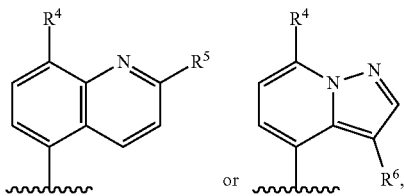

wherein

R⁴ is cyano;

R⁵ is H or deuterium; and

R⁶ is H or halogen.

5. The compound of claim 4, or a pharmaceutically acceptable salt thereof, wherein R⁶ is H or fluoro.

6. The compound of claim 4, or a pharmaceutically acceptable salt thereof, wherein Y is CH, and A is N; or Y is N, and A is CH.

7. The compound of claim 6, or a pharmaceutically acceptable salt thereof, wherein R³ is amino (C₁₋₆alkyl) azetidinyl; 3,4,4a,5,7,7a-hexahydro-2H-pyrrolo[3,4-b][1,4]oxazinyl; or amino (C₁₋₆alkoxy) pyrrolidinyl.

8. The compound of claim 7, or a pharmaceutically acceptable salt thereof, wherein R³ is 3-amino-3-methyl-azetidin-1-yl; 3,4,4a,5,7,7a-hexahydro-2H-pyrrolo[3,4-b][1,4]oxazin-6-yl; or 3-amino-4-methoxy-pyrrolidin-1-yl.

9. The compound of claim 3, wherein

R¹ is

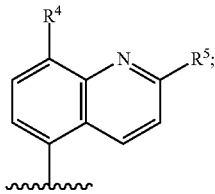

wherein

R⁴ is cyano;

R⁵ is deuterium;

R² is C₁₋₆alkyl;

R³ is amino (C₁₋₆alkyl) azetidinyl; 3,4,4a,5,7,7a-hexahydro-2H-pyrrolo[3,4-b][1,4]oxazinyl; or amino (C₁₋₆alkoxy) pyrrolidinyl; and Y is CH, and A is N; or Y is N, and A is CH;

or a pharmaceutically acceptable salt thereof.

10. The compound of claim 9, wherein

R² is methyl; and

R³ is 3-amino-3-methyl-azetidin-1-yl; 3,4,4a,5,7,7a-hexahydro-2H-pyrrolo[3,4-b][1,4]oxazin-6-yl; or 3-amino-4-methoxy-pyrrolidin-1-yl;

or a pharmaceutically acceptable salt thereof.

11. A compound selected from:

4-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

3-fluoro-4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile;

3-fluoro-4-[(2S,6R)-2-[[6-[[(3S,4R)-4-fluoropyrrolidin-3-yl]amino]spiro[1H-isobenzofuran-3,3'-azetidine]-1'-yl]methyl]-6-methyl-morpholin-4-yl]pyrazolo[1,5-a]pyridine-7-carbonitrile;

3-fluoro-4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile;

4-[(2S,6R)-2-[[6-[(3S)-3-amino-3-methyl-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile;

3-fluoro-4-[(2R,6S)-2-methyl-6-[(6-piperazin-1-ylspiro[1H-isobenzofuran-3,3'-azetidine]-1'-yl)methyl]morpholin-4-yl]pyrazolo[1,5-a]pyridine-7-carbonitrile;

4-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]pyrazolo[1,5-a]pyridine-7-carbonitrile;

4-[(2R,6S)-2-methyl-6-[[6-(6-methyl-2,6-diazaspiro[3.3]heptan-2-yl)spiro[1H-isobenzofuran-3,3'-azetidine]-1'-yl]methyl]morpholin-4-yl]pyrazolo[1,5-a]pyridine-7-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-[(3S,4S)-3-amino-4-hydroxy-pyrrolidin-1-yl]spiro[1H-isobenzofuran-3,3'-azetidine]-1'-yl]methyl]-6-methyl-morpholin-4-yl]-3-fluoro-pyrazolo[1,5-a]pyridine-7-carbonitrile;

5-[(2S,6R)-2-[[6-(3-amino-3-methyl-azetidin-1-yl)spiro[1H-isobenzofuran-3,3'-azetidine]-1'-yl]methyl]-6-methyl-morpholin-4-yl]-2-deuterio-quinoline-8-carbonitrile;

4-[(2S,6R)-2-[[6-(2,6-diazaspiro[3.3]heptan-2-yl)spiro[1H-isobenzofuran-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]-1-methyl-1,8-naphthyridin-2-one;

5-[(2S,6R)-2-[[6-(3-aminoazetidin-1-yl)spiro[1H-isobenzofuran-3,3'-azetidine]-1'-yl]methyl]-6-methyl-morpholin-4-yl]-2-deuterio-quinoline-8-carbonitrile;

2-deuterio-5-[(2R,6S)-2-methyl-6-[[6-(5-oxa-2,8-diazaspiro[3.5]nonan-2-yl)spiro[1H-isobenzofuran-3,3'-azetidine]-1'-yl]methyl]morpholin-4-yl]quinoline-8-carbonitrile;

5-[(2S,6R)-2-[[6-[(3R,4R)-3-amino-4-methoxy-pyrrolidin-1-yl]spiro[1H-isobenzofuran-3,3'-azetidine]-1'-yl]methyl]-6-methyl-morpholin-4-yl]-2-deuterio-quinoline-8-carbonitrile;

5-[(2S,6R)-2-[[6-[(4aR,7aR)-3,4,4a,5,7,7a-hexahydro-2H-pyrrolo[3,4-b][1,4]oxazin-6-yl]spiro[1H-isobenzofuran-3,3'-azetidine]-1'-yl]methyl]-6-methyl-morpholin-4-yl]-2-deuterio-quinoline-8-carbonitrile;

2-deuterio-5-[(2R,6S)-2-methyl-6-[(6-piperazin-1-yl-spiro[1H-isobenzofuran-3,3'-azetidine]-1'-yl)methyl]morpholin-4-yl]quinoline-8-carbonitrile;

4-[(2S,6R)-2-[[6-(3-aminoazetidin-1-yl)spiro[1H-isobenzofuran-3,3'-azetidine]-1'-yl]methyl]-6-methyl-morpholin-4-yl]pyrazolo[1,5-a]pyridine-7-carbonitrile;

5-[(2S,6R)-2-[[3-(3-aminoazetidin-1-yl)spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]-2-deuterio-quinoline-8-carbonitrile;

3-fluoro-4-[(2R,6S)-2-methyl-6-[[3-(6-methyl-2,6-diazaspiro[3.3]heptan-2-yl)spiro[5H-furo[3,4-b]pyridine-7,3'-azetidine]-1'-yl]methyl]morpholin-4-yl]pyrazolo[1,5-a]pyridine-7-carbonitrile;

5-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-2-deuterio-quinoline-8-carbonitrile;

4-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]-3-fluoro-pyrazolo[1,5-a]pyridine-7-carbonitrile;

4-[(2S,6R)-2-[[6-(3-amino-3-methyl-azetidin-1-yl)spiro[1H-furo[3,4-c]pyridine-3,3'-azetidine]-1'-yl]methyl]-6-methyl-morpholin-4-yl]pyrazolo[1,5-a]pyridine-7-carbonitrile;

4-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]pyrazolo[1,5-a]pyridine-7-carbonitrile;

5-[(2S,6R)-2-[[6-[(4aR,7aR)-3,4,4a,5,7,7a-hexahydro-2H-pyrrolo[3,4-b][1,4]oxazin-6-yl]spiro[1H-furo[3,4-c]pyridine-3,3'-azetidine]-1'-yl]methyl]-6-methyl-morpholin-4-yl]-2-deuterio-quinoline-8-carbonitrile;

5-[(2S,6R)-2-[[3-[(4aR,7aR)-3,4,4a,5,7,7a-hexahydro-2H-pyrrolo[3,4-b][1,4]oxazin-6-yl]spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[3-[(3R,4R)-3-amino-4-methoxy-pyrrolidin-1-yl]spiro[5H-furo[3,4-b]pyridine-7,3'-azetidine]-1'-yl]methyl]-6-methyl-morpholin-4-yl]-2-deuterio-quinoline-8-carbonitrile;

5-[(2S,6R)-2-[[6-(3-aminoazetidin-1-yl)spiro[1H-furo[3,4-c]pyridine-3,3'-azetidine]-1'-yl]methyl]-6-methyl-morpholin-4-yl]-2-deuterio-quinoline-8-carbonitrile; and 4-[(2S,6R)-2-[[3-(3-amino-3-methyl-azetidin-1-yl)spiro[5H-furo[3,4-b]pyridine-7,3'-azetidine]-1'-yl]methyl]-6-methyl-morpholin-4-yl]-3-fluoro-pyrazolo[1,5-a]pyridine-7-carbonitrile;

or a pharmaceutically acceptable salt thereof.

12. A process for the preparation of a compound of claim 1, the process comprising the following step:
the reaction of compound of formula (VII),

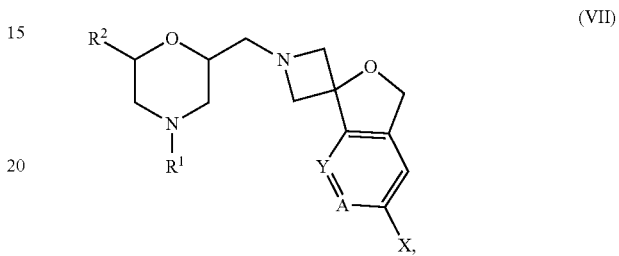

(VII)

and
amine HR³ (VIII) via Buchwald-Hartwig amination, wherein
X is halogen; and
R¹, R², R³, Y and A are defined as in claim 1,
to produce the compound of claim 1.

13. A pharmaceutical composition comprising a compound of claim 1, or a pharmaceutically acceptable salt thereof, and a therapeutically inert carrier.

14. A compound of formula (I), or pharmaceutically acceptable salt thereof, manufactured according to the process of claim 12.

15. A method for the treatment of systemic lupus erythematosus or lupus nephritis in a human mammal in need thereof, which method comprises administering a therapeutically effective amount of a compound of claim 1, or a pharmaceutically acceptable salt thereof, to the human mammal.

16. A pharmaceutical composition comprising a compound of claim 11, or a pharmaceutically acceptable salt thereof, and a therapeutically inert carrier.

17. A method for the treatment of systemic lupus erythematosus or lupus nephritis in a human mammal in need thereof, which method comprises administering a therapeutically effective amount of a compound of claim 11, or a pharmaceutically acceptable salt thereof, to the human mammal.

* * * * *